(12) United States Patent
Boucly et al.

(10) Patent No.: US 8,481,956 B2
(45) Date of Patent: Jul. 9, 2013

(54) DENTAL RADIOLOGY APPARATUS AND SIGNAL PROCESSING METHOD USED THEREWITH

(75) Inventors: Alain Boucly, Chauconin-Neufmontiers (FR); Jean-Marc Inglese, Bussy Saint Georges (FR); Philippe Congy, Meaux (FR)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/617,217

(22) Filed: Sep. 14, 2012

(65) Prior Publication Data

US 2013/0020490 A1  Jan. 24, 2013

Related U.S. Application Data

(60) Continuation of application No. 13/188,497, filed on Jul. 22, 2011, now Pat. No. 8,319,190, which is a continuation of application No. 12/505,556, filed on Jul. 20, 2009, now Pat. No. 8,008,628, which is a division of application No. 10/580,395, filed as application No. PCT/EP2004/012885 on Nov. 13, 2004, now Pat. No. 7,608,834.

(30) Foreign Application Priority Data

Nov. 21, 2003 (EP) ..................... 03292901

(51) Int. Cl.
*G01T 1/20* (2006.01)
*H01L 27/146* (2006.01)
*A61B 6/14* (2006.01)
*G03B 42/02* (2006.01)

(52) U.S. Cl.
USPC .................. 250/370.09; 250/370.11; 378/38; 378/168; 378/169; 378/170

(58) Field of Classification Search
USPC ........... 250/370.09, 370.11; 378/38, 168–170
See application file for complete search history.

(56) References Cited

U.S. PATENT DOCUMENTS 4,342,086 A  7/1982  Adib
4,366,382 A  12/1982  Kotowski
(Continued)

FOREIGN PATENT DOCUMENTS

DE  44 41 939 A1  6/1995
DE  197 34 717 A1  2/1999
(Continued)

OTHER PUBLICATIONS

Mahito Shinohara et al., "A bipolar imager with bipolar field memory," Proc. 1997 IEEE Workshops on CCDs and Advanced Images Sensors, Jun. 5-7, 1997, Burges, Belgium.

(Continued)

*Primary Examiner* — David Porta
*Assistant Examiner* — Mindy Vu

(57) ABSTRACT

A dental radiology apparatus having: an intraoral sensor comprising a detector including an active pixel array produced using biCMOS technology and converting a received x-ray into at least one analog electrical output signal; an electronic module encapsulated in a case and which has at least one detector activation device, the module linked to the sensor for the transmission to the sensor of a detector activation signal generated in the module and for the transmission to the module of the at least one analog electrical output signal, the module having analog-digital means for converting the at least one analog electrical output signal into at least one digital output signal. A remote processing and display unit of the at least one digital output signal is linked to the electronic module to ensure the transmission to the unit of the at least one digital output signal.

18 Claims, 9 Drawing Sheets

U.S. PATENT DOCUMENTS

| | | | |
|---|---|---|---|
| 4,409,616 A | 10/1983 | Ledley | |
| 4,593,400 A | 6/1986 | Mouyen | |
| 5,189,528 A | 2/1993 | Takashima et al. | |
| 5,434,418 A | 7/1995 | Schick | |
| 5,510,623 A * | 4/1996 | Sayag et al. | 250/370.11 |
| 5,519,437 A | 5/1996 | Nelvig | |
| 5,572,566 A | 11/1996 | Suzicki et al. | |
| 5,604,781 A | 2/1997 | Suzuki et al. | |
| 5,677,940 A | 10/1997 | Suzuki et al. | |
| 5,894,129 A * | 4/1999 | Pool | 250/370.09 |
| 5,912,942 A | 6/1999 | Schick et al. | |
| 5,933,107 A | 8/1999 | Tan | |
| 6,055,292 A | 4/2000 | Zeller et al. | |
| 6,069,935 A | 5/2000 | Schick et al. | |
| 6,134,298 A | 10/2000 | Schick et al. | |
| 6,144,408 A | 11/2000 | MacLean | |
| 6,351,519 B1 | 2/2002 | Bonk et al. | |
| 6,404,854 B1 | 6/2002 | Carroll et al. | |
| 6,497,511 B1 * | 12/2002 | Schmitt et al. | 378/207 |
| 6,549,235 B1 | 4/2003 | Fossum et al. | |
| 6,972,411 B2 * | 12/2005 | Schick et al. | 250/370.11 |
| 7,612,803 B2 | 11/2009 | Meitav et al. | |
| 2002/0070365 A1 | 6/2002 | Karellas | |
| 2003/0146987 A1 | 8/2003 | Prentice et al. | |
| 2004/0000630 A1 | 1/2004 | Spartiotis et al. | |
| 2004/0038169 A1 | 2/2004 | Mandelkern et al. | |

FOREIGN PATENT DOCUMENTS

| | | |
|---|---|---|
| EP | 0 129 451 | 12/1987 |
| EP | 0 854 639 A2 | 7/1998 |
| EP | 0 858 111 | 8/1998 |
| EP | 0 562 657 B1 | 9/1998 |
| EP | 0 957 628 A2 | 11/1999 |
| FR | 2 547 495 | 6/1983 |
| FR | 2 797 760 | 3/2001 |
| GB | 2 371 196 | 7/2002 |
| JP | 07-015666 | 1/1995 |
| JP | 07-148161 A | 6/1995 |
| JP | 07-322141 | 12/1995 |
| JP | 11-188033 A | 7/1999 |
| JP | 2001-174565 | 6/2001 |
| JP | 2002-344813 A | 11/2002 |
| JP | 2002-528728 | 3/2003 |
| JP | 2003-79617 A | 3/2003 |
| JP | 2003-209748 | 7/2003 |
| WO | WO 89/10037 | 10/1989 |
| WO | WO 93/23952 | 11/1993 |
| WO | WO 98/20616 | 5/1998 |
| WO | WO 00/29872 | 5/2000 |
| WO | WO 02/052505 | 7/2002 |
| WO | WO 03/032839 | 4/2003 |

OTHER PUBLICATIONS

Hamamatsu Preliminary Data, Hamamatsu Photonics K.K., Cat. No. KMPD1022E02, Mar. 1998, printed in Japan, pp. 6.

European Search Report, Application No. EP 03 29 2901, Apr. 5, 2004, pp. 5—French text.

European Search Report, Application No. EP 07 00 5766, May 29, 2007, pp. 5.

European Search Report, Application No. EP 07 00 5767, Jun. 15, 2007, pp. 5.

European Search Report, Application No. EP 07 00 5769, Jul. 20, 2007, pp. 3.

International Search Report, PCT/EP2004/012885, Feb. 7, 2005 (3 pages).

* cited by examiner clk-x

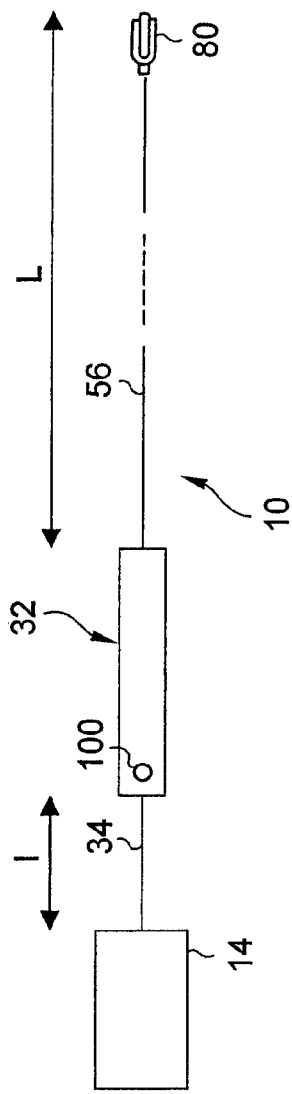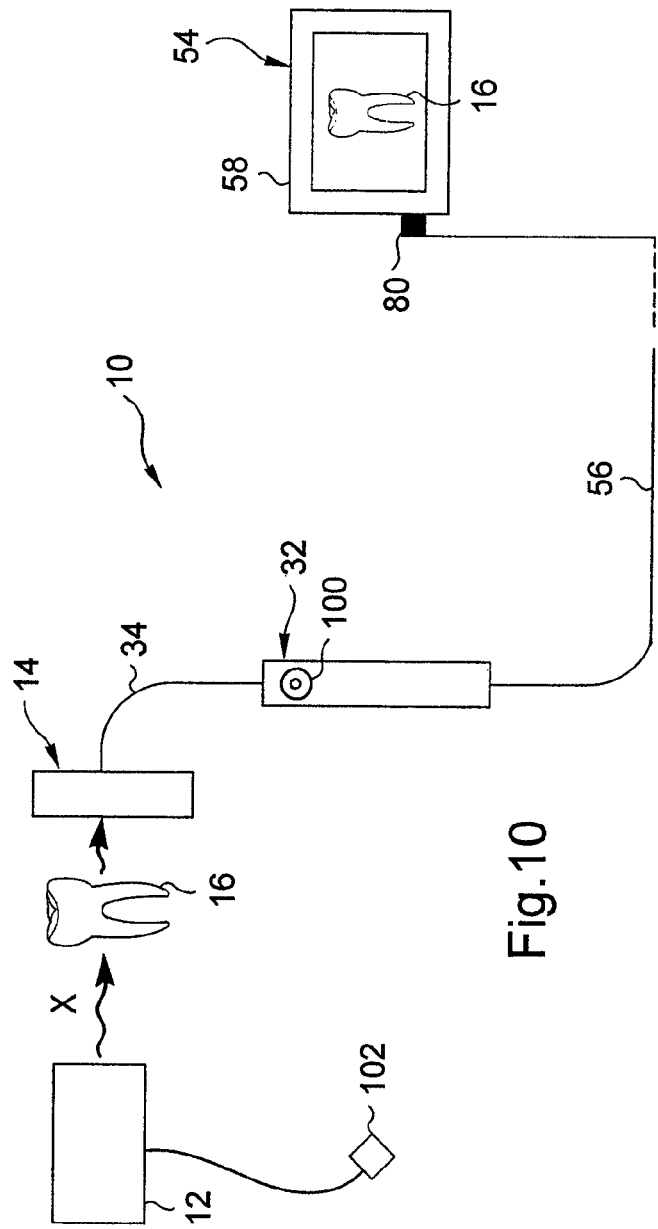
Fig. 9
Fig. 10

DENTAL RADIOLOGY APPARATUS AND SIGNAL PROCESSING METHOD USED THEREWITH

CROSS REFERENCE TO RELATED APPLICATIONS

This is a Continuation of U.S. Ser. No. 13/188,497 now U.S. Pat. No. 8,319,190 titled DENTAL RADIOLOGY APPARATUS AND SIGNAL PROCESSING METHOD USED THEREWITH filed on Jul. 22, 2011 in the names of Boucly et al, which was a Continuation of U.S. Ser. No. 12/505,556 titled DENTAL RADIOLOGY APPARATUS AND SIGNAL PROCESSING METHOD USED THEREWITH filed on Jul. 20, 2009 in the names of Boucly et al, which issued as U.S. Pat. No. 8,008,628, which was a Divisional Application of U.S. Ser. No. 10/580,395 titled DENTAL RADIOLOGY APPARATUS AND SIGNAL PROCESSING METHOD USED THEREWITH filed on Apr. 27, 2007 in the names of Boucly et al, which issued as U.S. Pat. No. 7,608,834, which claims priority to PCT/EP2004/012885 filed on Nov. 13, 2004, which claims priority to EP 03292901.0 filed Nov. 21, 2003.

FIELD OF THE INVENTION

The invention relates to the field of dental radiology.

BACKGROUND OF THE INVENTION

Dental radiology equipment as described in French patent FR 2,547,495 and European patent No. 0,129,451 is known.

Such equipment comprises an x-ray source that emits radiation directed to a tooth located in a patient's mouth and behind which is an intraoral sensor that receives the x-rays that have passed through the tooth.

This sensor comprises: a scintillator on entry to convert the x-rays that have passed through the tooth into visible light; and a fiber optic plate to transmit the converted visible light to a charge-coupled device CCD-type detector, which converts the converted visible light into an analog electrical signal, while absorbing the residual x-rays that have not been converted into visible light.

The electrical signal is amplified and transmitted in analog form through a long cable, to a remote processing and display workstation where the signal is digitized and processed to produce an image that is then viewed on a display screen.

This type of equipment with a charge-coupled device detector creates a high signal-to-noise ratio (SNR), for example, of about 60 dB.

Also known, according to U.S. Pat. No. 5,912,942, is a type of x-ray detector wherein the active pixel sensor (APS) uses CMOS manufacturing technology.

In the above-mentioned patent, the radiology equipment described therein comprises: a source of x-rays passing through an object, a scintillator that converts the x-rays that have passed through the object into visible light, and a fiber optic plate that transmits the converted visible light to an active pixels array that converts it into an analog electrical signal.

It can be observed that the CMOS detector obtains a signal-to-noise ratio (SNR) of inferior quality to that of the CCD detector.

Several factors have thus been identified that limit the signal-to-noise ratio of the CMOS detector.

Among these factors, is the dark current that can be defined as being the electrical current collected at the detector output when the latter is not exposed to any x-ray.

The presence of the dark current leads to a deterioration of the signal-to-noise ratio.

It may be noted that, insofar as the intensity of the dark current has the special feature of considerably increasing with temperature and as the detector heats during its use, it is advisable to cool it and/or not operate it for too long a period so as not to further deteriorate the signal-to-noise ratio.

A second limiting factor is the detector's fill factor.

For a CCD detector, the fill factor is in theory 1, which means that the whole pixel surface is used to capture the x-rays and produce the corresponding electrical charge that will contribute to forming the image of the x-rayed tooth.

On the contrary, in a CMOS active pixel detector, the active element of the pixel occupies part of the pixel surface, without however contributing to the capture of the x-ray.

With part of the pixel not contributing to the fill, i.e. not contributing to the photon-electron conversion, the fill factor is less than 1, which hinders obtaining a good signal-to-noise ratio.

A third limiting factor results from the fact that today we do not know how to use CMOS technology to make large size monolithic active pixel arrays, typically about 20×30 mm, which are the commonly used dimensions for dental radiology sensors.

To obtain a large-size active pixel array in CMOS technology, it is necessary to assemble together several smaller-size sub-arrays by "stitching".

The unevenness created by an array obtained in this way contributes to deteriorating the signal-to-noise ratio.

Further, it should be noted that the conditions specific to the field of dental radiology make the design of dental radiology apparatus with a high quality signal-to-noise ratio particularly difficult.

In particular, insofar as people are exposed to x-rays, the x-ray doses used should be as low as possible and these people should be exposed to the x-rays for the shortest possible time.

In other fields where a CMOS technology x-ray detector is used, the x-ray doses are not required to be as low as in dental radiology, which enables a higher intensity signal at the detector output, and thus a better signal-to-noise ratio.

Also, one of the special features of intraoral dental radiology sensors stems from the fact that the sensor that is placed in a patient's mouth has to be as small as possible to limit the discomfort caused to the patient, which implies reducing the number of components in the sensor.

It may be noted that, in a preferred embodiment of the x-ray detectors described in U.S. Pat. No. 5,912,942, the sensor comprises an integral analog-digital converter in order to digitize the analog output signal that is to be transmitted to the remote computer without delay.

Detector design like this goes against the miniaturization required for installation in a patient's mouth.

In addition, the introduction of an analog-digital converter alongside a CMOS technology active pixel array, which is an analog element, constitutes an additional source of noise which, added to the constraint of a minimal dose of x-rays, contributes to deteriorating the detector's signal-to-noise ratio.

Other unmentioned sources of noise may be noted that are also capable of affecting the detector's signal-to-noise ratio.

Generally, there is a need for new dental radiology apparatuses and signal processing methods used therein, which can improve the signal-to-noise ratio provided by the apparatus's detector.

It is also apparent that the use of existing dental radiology apparatuses causes hygiene problems that it would be desirable to solve, at least to some extent.

Thus, when the dentist wearing surgical gloves places an intraoral sensor behind a tooth in a patient's mouth, said sensor comprising one of the detector types mentioned above, he/she has to switch on the sensor and then start the x-ray generator.

To do this, he/she has to go to the computer located a few meters away, which is already not very practical, and then click on a computer mouse to start the sensor and the x-ray generator by means of a programmed interface.

However, at this time, the dentist is wearing gloves that are already contaminated by the patient's saliva, which risks causing cross-contamination when the dentist later handles the computer mouse using gloves impregnated with another patient's saliva.

Faced with such a situation, the dentist has then either to remove the gloves before handling the mouse, or disinfect them after use, which in both cases represents additional constraints that quickly become onerous when they are repeated several dozen times a day.

On the other hand, there is also a need to have dental radiology apparatus as small as possible, especially for the intraoral sensor and related electronics.

Thus the invention aims to remedy at least one of the above-mentioned problems.

SUMMARY OF THE INVENTION

According to a first aspect, the invention relates to a dental radiology apparatus, characterized in that it comprises: an intraoral sensor comprising a detector that includes an active pixel array produced using biCMOS technology and converting received x-rays into at least one analog electrical output signal, an electronic module encapsulated in a case and which comprises at least one detector activation device, the module being linked to the sensor by a wire link for the transmission to said sensor of a detector activation signal generated in the module and for the transmission to the module of said at least one analog electrical output signal, the module having analog-digital means of conversion of said at least one analog electrical output signal into at least one digital output signal, and a remote processing and display unit of said at least one digital output signal which is linked to the electronic module by a wire link intended to ensure the transmission to the unit of said at least one digital output signal.

According to this aspect of the invention, the electronic module has at least one detector activation device and is sufficiently close to the sensor to be handled by a dentist during the intervention with a patient and thus enable, by using the activation device by hand, or with a foot if the module is located on the floor, the sensor to be switched on for the purpose of taking an image of a tooth.

Insofar as the electronic module equipped with the activation device is located within the dentist's sphere of activity, this saves him/her from having to move as far as the processing and display unit which in practice is several meters away from said dentist.

Similarly, this precludes the problems of cross-contamination that may arise if the dentist has to move as far as the remote processing and display unit to handle a sensor activation device such as a computer mouse by means of a programmed interface.

Assuming the computer mouse has to be disinfected, this additional disinfection operation is also avoided.

Further, the nearness of the electronic module to the sensor means that a relatively short wire link can be used (generally less than one meter), which means not deteriorating the detector's signal-to-noise ratio.

The activation device also enables the remote control of certain functions that the dentist may have to use immediately before or after taking the image, with the same hygiene constraints. Among these functions, mentioned non-exhaustively, are turning the image for maxillary/mandibular orientation, or adjusting display settings such as contrast and brightness.

This aspect of the invention is particularly simple to implement.

It may be noted that the case has an overall elongated shape which allows it to be easily handled and cleaned.

According to one characteristic, the encapsulated electronic module has weight and dimensions suited to enable, when the apparatus is used, the sensor to be held in a patient's mouth when said encapsulated electronic module is suspended from said sensor.

According to one characteristic, the electronic module is at a distance between 50 cm and 2 m from the sensor.

According to one characteristic, the encapsulated electronic module is nearer the sensor than the processing and display unit.

According to one characteristic, said at least one activation device is a pushbutton.

According to one characteristic, each wire link is a cable.

According to one characteristic, as each cable is inserted at one of its ends into the case, the electronic module is fitted with anti-pull devices that are each capable of working with one end of one of the cables to prevent the removal of the corresponding cable from the case by a pulling action exerted on said cable.

These anti-pull devices prevent the use of electrical connectors that can cause false contacts and risk disconnecting unexpectedly.

According to one characteristic, as each cable has a coaxial sheath with a bundle of electrical wires, opposite the end of each cable that inserts into the case, the part of the corresponding wire bundle is held solid with a metal anti-pull body of the corresponding anti-pull device.

According to one characteristic, the electronic module comes in the form of a printed circuit with overall elongated shape along a longitudinal axis and having, at each of the two opposite ends arranged longitudinally, an axial cut-out open to the outside of the circuit to house in the longitudinal direction a metal anti-pull body and the part of the corresponding wire bundle made solid and aligned, the cut-out being arranged to prevent removal of the body in this longitudinal direction.

According to one characteristic, each metal anti-pull body is provided with fitting elements arranged on the opposite sides parallel to the direction of the part of the wire bundle made solid with the body and which work together with the complementary fitting elements respectively arranged on the opposite longitudinal edges of the corresponding cut-out.

According to one characteristic, each part of each of the wire bundles made solid with an anti-pull body is held solid with a cylindrical drum that, on the one hand, surrounds the anti-pull body and, on the other hand, is solid with the corresponding body.

According to one characteristic, each part of each of the wire bundles made solid with an anti-pull body is welded directly or indirectly to the latter.

According to one characteristic, two metal half-shells are arranged on either side of the printed circuit board and assembled together to secure said printed circuit board.

These half-shells protect the electronic module mechanically.

According to one characteristic, the case has at least two plastic parts forming a cover and which are assembled together to encapsulate the electronic module.

According to one characteristic, the case has an external surface that can be disinfected.

According to one characteristic, the shapes of the external surface are designed to prevent the incrustation of dirt.

According to one characteristic, the external surface is drip-proof.

According to one characteristic, the wire link between the electronic module and the processing and display unit complies with standard USB2.0 or can also enable transmission speeds greater than those of the above-mentioned standard.

According to one characteristic, the sensor has an x-ray converter that is capable of converting the x-rays that have passed through a tooth into visible light.

According to one characteristic, the biCMOS detector including the active pixel array is capable of converting at least one part of the visible light coming from the conversion of the x-rays into at least one analog electrical output signal.

According to a second aspect, the invention relates to a dental radiology apparatus, characterized in that it comprises an intraoral sensor intended to receive x-rays that have passed through at least one tooth, said sensor including: an x-ray to visible light converter, a detector comprising an active pixel array produced using biCMOS technology on a substrate made of semi-conductor material, and a sequencer capable of generating several control signals to control the active pixel array, said sequencer being integrated on the same substrate as the array.

By integrating the sequencer on the same silicon chip as the array and not in offset electronic equipment, a reduced number of electrical signals are required to operate the sequencer and the array and that have to be received from outside the sensor, which is particularly advantageous because there are thus fewer external signals to be produced.

This therefore enables the risks of pollution of these signals during their transmission to be reduced, which contributes to not deteriorating the detector's signal-to-noise ratio.

Furthermore, integration of the sequencer on the same silicon chip as the array enables a detector of minimum size and simplified electronic interface to be produced, which would not be the case if the sequencer were a separate component.

According to one characteristic, the sequencer is capable of receiving at least one signal external to the sensor, which the generated control signals are based on.

Thus, for example, the sequencer is capable of receiving a single clock signal which most of the array's internal signals derive from.

According to one characteristic, the apparatus has an electronic module separate from the sensor and which is capable of generating said at least one signal external to the sensor, which the generated control signals are based on.

According to one characteristic, the apparatus has a link between the electronic module and the sensor for the transmission of said at least one external signal.

Advantageously, the number of signals transmitted from the module to the sensor remains reasonable because of the sequencer's organization.

According to one characteristic, the link is a wire link.

According to a third aspect, the invention relates to a signal processing method in a dental radiology apparatus comprising an intraoral sensor that includes an active pixel array produced using biCMOS technology, characterized in that the method has the following steps: sampling of the data values held by the pixels of the array having been exposed to x-rays, generation of at least one sensor analog output signal based on the data values sampled on the pixels, conversion of said at least one sensor analog output signal into one digital output signal, and application of a correction to the analog output signal or to one of the analog output signals, to compensate in the digital output signal for any drifts due to the variations of the dark current in the array.

In conjunction with this, the invention also targets a dental radiology apparatus, characterized in that it comprises an intraoral sensor including: a detector comprising an active pixel array produced using biCMOS technology and converting x-rays received by the array into at least one analog output signal, the apparatus comprising an analog-digital converter for converting said at least one analog output signal into one digital output signal, a signal corrector that is designed to apply a correction to the analog output signal or to one of the analog output signals, to compensate in the digital output signal for any drifts due to the variations of the dark current in the array.

According to this aspect of the invention, a correction is made to the analog output signal delivered by the sensor so that, in the digital output signal obtained following conversion of the corrected analog signal, any drifts due to the variations of the dark current in the array are compensated for.

As the dark current increases especially by heating during the array's operating time, this enables an optimum adjustment of the analog chain to be conserved over time.

This aspect of the invention prevents having to over accelerate the reading of the array, which could lead to the generation of reading noise that deteriorates the detector's signal-to-noise ratio.

According to one characteristic, the application step of a correction takes account of at least one value of a correction signal that is generated from the data values sampled on the array's pixels when it is not exposed to any radiation.

According to one characteristic, the correction signal is generated between two array exposure phases to radiation.

According to one characteristic, the correction signal is generated regularly over time, or even irregularly.

According to one characteristic, the method comprises steps of generation and analog-digital conversion of a correction and sensor output analog signal prior to the step of correction application.

According to one characteristic, the method comprises a step of digital-analog conversion of at least one value of the digital correction signal into an analog correction signal that is applied to the analog output signal or to one of the analog output signals.

According to one characteristic, the method comprises a step of producing a single analog output signal based on two symmetrical analog output signals.

According to one characteristic, the method comprises a step of producing a single analog output signal based on two analog output signals, following the step of correction application to one of the two signals.

According to one characteristic, the step of producing a single analog output signal based on two analog output signals is a summing step of the two analog output signals.

It may be noted that producing a single signal is, for example, performed in an analog-digital converter.

According to one characteristic, the step of correction application to the analog output signal or to one of the analog output signals is adjusted according to the law of variation in relation to the time of the dark current of the CMOS active pixel array and the duration of using this array.

According to one characteristic, the method comprises a step of transmission of said at least one analog output signal to a electronic module remote from the sensor, the conversion and correction application steps being performed in said remote module.

According to one characteristic, reading the array's pixels is preferably carried out at an adjusted speed that enables the array to be read sufficiently fast to avoid deteriorating the detector's signal-to-noise ratio, but not so fast as to introduce any reading noise.

According to one characteristic, the method comprises a transmission step of the compensated digital output signal from the remote electronic module to a remote signal processing and display unit.

According to one characteristic, the transmission is carried out using a wire link enabling a transmission speed at least equal to that of standard USB2.0.

According to one characteristic, the method comprises a prior step of reception by the sensor of x-rays having passed through at least one tooth.

According to one characteristic, the method comprises a later step of conversion into visible light of the received x-rays, the array's pixels being exposed to visible light.

According to a fourth aspect, the invention relates to a dental radiology apparatus, characterized in that it comprises an intraoral sensor intended to receive x-rays that have passed through at least one tooth, said sensor comprising: an x-ray to visible light converter, a detector comprising an active pixel array produced using biCMOS technology and converting the visible light thus converted into at least one analog electrical signal, a generator of a sampling signal synchronized with said at least one analog electrical signal and which is intended for the later conversion of said at least one analog electrical signal into a digital signal.

In conjunction with this, the invention also targets a signal processing method in a dental radiology apparatus comprising an intraoral sensor intended to receive x-rays that have passed through at least one tooth, characterized in that it includes the following steps performed in the sensor: reception of x-rays having passed through at least one tooth, conversion of the received x-rays into visible light, conversion of the visible light thus converted into at least one analog electrical signal by an active pixel array produced using biCMOS technology, generation of a sampling signal synchronized with said at least one analog electrical signal and which is intended for the later conversion of said at least one analog electrical signal into a digital signal.

According to this aspect of the invention, the fact of generating a sampling signal synchronized with the analog signal supplied by the detector will enable the sampling signal synchronized with the detector's analog signal to be transmitted simultaneously for the purposes of the later analog-digital conversion of said analog signal.

By transmitting these two signals simultaneously, any disturbance and/or phase difference affecting one of the signals during the transmission will inevitably affect the other signal and will thus be compensatable.

Further, this aspect of the invention is advantageous because it is simpler to implement than a technique according to which the clock required for sampling the analog signal for its conversion is produced locally at the offset converter. Indeed, the clock has to be produced in advance and take account of the various delays that affect the analog signal during its transmission, which can be problematic if these delays vary over time.

According to this aspect of the invention, on the contrary, whatever the delays and whatever their variation over time, they are by definition compensatable as they affect both signals.

The signal processing according to the invention is thus more reliable than in the prior art.

According to one characteristic, the apparatus comprises: an electronic module remote from the sensor, a link between the electronic module and the sensor for the simultaneous and in phase transmission of said at least one electrical signal and of the sampling signal.

According to one characteristic, the electronic module comprises an analog-digital converter for converting said at least one analog electrical signal into one digital signal based on the sampling signal.

According to one characteristic, the link between the electronic module and the sensor is a wire link.

According to one characteristic, the apparatus comprises a signal generator which is capable of generating, based on one analog electrical signal from the detector, two differential analog electrical signals.

The transmission of these two differential signals enables later compensation for disturbances arising on the link and that affect both signals.

According to one characteristic, the signal generator is integrated into the sensor, the link ensuring the simultaneous and in phase transmission of the two differential analog electrical signals and the sampling signal.

According to one characteristic, the sensor comprises a sequencer that is capable of generating several active pixel array control signals and which includes the sampling signal generator.

According to one characteristic, reading the array's pixels is preferably carried out at an adjusted speed that enables the array to be read sufficiently fast to avoid deteriorating the detector's signal-to-noise ratio, but not so fast as to introduce any reading noise.

According to a fifth aspect, the invention relates to a signal processing method in a dental radiology apparatus comprising an intraoral sensor that includes a detector including an active pixel array produced using biCMOS technology, the pixels being arranged in rows and columns, characterized in that it comprises the following steps: selection of each row of the array, for each row selected, sampling of the data values held by each pixel having been exposed to radiation, generation of a read signal from the sampled data values for the array's pixels, application at the detector's input of an input reference signal (black-in), production of an output signal from the array's read signal and an output reference signal (black ref) representative of the detector's intrinsic electronic drifts and which is obtained at the detector output based on the input reference signal applied at said detector's input.

In conjunction with this, the invention also targets a dental radiology apparatus comprising an intraoral sensor that includes a detector including an active pixel array produced using biCMOS technology, the pixels being arranged in rows and columns, characterized in that it comprises: means for selecting each row of the array, means for sampling the data values held by each pixel having been exposed to radiation, for each row selected, means for generating a read signal based on the sampled data values for the array's pixels, means for applying at the detector's input an input reference signal, means for producing an output signal from the array's read signal and an output reference signal (black ref) representative of the detector's intrinsic electronic drifts and which is obtained at the detector output based on the input reference signal applied at said detector's input.

According to this aspect of the invention, the use of a reference signal representative of the detector's intrinsic electronic drifts enables compensation in the detector's output signal for the drifts specific to the detector's manufacture (dispersions during manufacture) but which vary from one detector to another.

In this way, the signal-to-noise ratio supplied by the detector is improved compared with the techniques provided for in the prior art.

According to one characteristic, the output signal is produced by forming a difference between the array's read signal and the output reference signal (black ref), which enables the above-mentioned drifts to be dealt with.

According to one characteristic, for each array row selected, after the first sampling step, the method includes a second sampling step of the data values obtained after resetting each pixel.

According to one characteristic, the method includes a step of applying a resetting signal to each selected row between the two sampling steps.

According to one characteristic, the array read signal is generated by forming the difference between the data values held by the array's pixels and obtained respectively after each sampling of the same pixel.

According to one characteristic, the input reference signal is DC voltage.

According to one characteristic, the method includes a step of receiving the input reference signal that comes from an electronic module remote from the sensor.

According to one characteristic, prior to the first sampling step, the pixel array is exposed to visible light coming from the conversion of x-rays that have passed through a tooth.

According to one characteristic, the output signal that is produced is an analog output signal.

According to one characteristic, the analog output signal is delivered by the sensor.

According to one characteristic, the method includes a step of converting the analog output signal into a digital output signal.

According to one characteristic, the method includes a step of transmitting the output signal to an electronic module remote from the sensor.

According to one characteristic, the conversion step is performed in the electronic module.

According to one characteristic, reading the array's pixels is preferably carried out at an adjusted speed that enables the array to be read sufficiently fast to avoid deteriorating the detector's signal-to-noise ratio, but not so fast as to introduce any reading noise.

According to a sixth aspect, the invention relates to a signal processing method in a dental radiology apparatus comprising an intraoral sensor that includes an active pixel array produced using biCMOS technology, the pixels being arranged in rows and columns, the sensor delivering an analog output signal produced from the data values held by the array's pixels exposed to radiation, characterized in that, the pixels of at least one array column being optically inactive, the method includes the following steps: conversion of the analog output signal into a digital output signal, reading in the digital output signal of one or more data values coming from each optically inactive pixel of an array row, reading in the digital output signal of one or more data values coming from each optically inactive pixel of at least one adjacent row, the relevant pixel(s) of each of the two rows being equal in number and arranged in the same column(s), comparison of the data value(s) read respectively for the inactive pixel(s) of a row with the data value(s) read respectively for the inactive pixel(s) of said at least one adjacent row, according to the result of the comparison, decision-making as to any modification in the output signal of the data values of all the pixels of one of the rows used for the comparison.

In conjunction with this, the invention also targets a dental radiology apparatus comprising an intraoral sensor that includes an active pixel array produced using biCMOS technology, the pixels being arranged in rows and columns, the sensor delivering an analog output signal produced from the data values held by the array's pixels exposed to radiation, characterized in that the pixels of at least one array column being optically inactive, the apparatus includes: means for converting the analog output signal into a digital output signal, means for reading, in the digital output signal, one or more data values coming from each optically inactive pixel of an array row, means for reading, in the digital output signal, one or more data values coming from each optically inactive pixel of at least one adjacent row, the relevant pixel(s) of each of the two rows being equal in number and arranged in the same column(s), a comparator supplying a comparison of the data value(s) read respectively for the inactive pixel(s) of a row with the data value(s) read respectively for the inactive pixel(s) of said at least one adjacent row, decision-making means capable of providing a decision as to any modification in the output signal of the data values of all the pixels of one of the rows used for the comparison.

According to this aspect, the sensor's digital output signal is processed by correcting, if necessary, the data values from the pixels of one or more array rows to prevent the introduction of additional drifts in the signal, which would risk deteriorating the latter's signal-to-noise ratio in a way that is particularly visible on the image.

Indeed, the deterioration would be shown by horizontal streaking of the image due to an average noise value varying from one row to another.

According to one characteristic, when the data values compared with one another are different from one row to another, the method includes a modification step, in the output signal, of the data value of each pixel of the array's adjacent row.

This enables readjustment of the average level of the pixels of the corresponding row.

According to one characteristic, the array rows are compared two by two.

According to one characteristic, when two consecutive array rows are compared, the modification is applied to the data values of the pixels of the second row.

According to one characteristic, the method includes the following steps: reading of the data values $S_i(n)$, i=1 to m, coming respectively from a number m of optically inactive pixels of a first array row, reading of the data values $S_i(n+1)$ coming respectively from m optically inactive pixels of a second row which is the next row of the array, determining for each of the first and second rows an average data value $\overline{S}(n)$, $\overline{S}(n+1)$ being obtained from the respective data values $S_i(n)$, $S_i(n+1)$ of each row, comparing the average data values $\overline{S}(n)$, and $\overline{S}(n+1)$ one with another, according to the result of the comparison, decision-making as to any modification, in the output signal, of the data values of all the pixels of the second row.

According to one characteristic, when the compared average data values differ one from another, the method includes a modification step of the data value of each pixel of the second row by assigning to each of these data values the difference between the average data values S(n), and $\overline{S}$(n+1) to adjust the average data value $\overline{S}$(n+1) of the second row to the average data value $\overline{S}$(n) of the first row.

According to one characteristic, the method includes a step of transmitting the analog output signal to an electronic module remote from the sensor, prior to the steps of reading the data values.

According to one characteristic, the conversion step of the analog output signal is performed in the electronic module.

According to one characteristic, the method includes a prior step of reception by the sensor of x-rays having passed through at least one tooth.

According to one characteristic, the method includes a later step of conversion into visible light of the received x-rays, the array's pixels being exposed to visible light.

According to one characteristic, reading the array's pixels is preferably carried out at an adjusted speed that enables the array to be read sufficiently fast to avoid deteriorating the detector's signal-to-noise ratio, but not so fast as to introduce any reading noise.

BRIEF DESCRIPTION OF THE DRAWINGS

Other characteristics and advantages will appear during the following description, given solely as a non-limiting example and with reference to the appended drawings.

FIG. 2 is a partial schematic view of the dental radiology apparatus according to the invention and that completes the representation of FIG. 1a.

FIG. 9 is a general schematic view of the removable part of the dental radiology apparatus according to the invention and that is represented as deployed.

FIG. 10 is a situational view of the dental radiology apparatus according to the invention during the taking of an image of a tooth.

DETAILED DESCRIPTION OF THE INVENTION

This is a Continuation of U.S. Ser. No. 13/188,497 titled DENTAL RADIOLOGY APPARATUS AND SIGNAL PROCESSING METHOD USED THEREWITH filed on Jul. 22, 2011 in the names of Boucly et al, which was a Continuation of U.S. Ser. No. 12/505,556 titled DENTAL RADIOLOGY APPARATUS AND SIGNAL PROCESSING METHOD USED THEREWITH filed on Jul. 20, 2009 in the names of Boucly et al, which issued as U.S. Pat. No. 8,008,628, which was a Divisional Application of U.S. Ser. No. 10/580,395 titled DENTAL RADIOLOGY APPARATUS AND SIGNAL PROCESSING METHOD USED THEREWITH filed on Apr. 27, 2007 in the names of Boucly et al, which issued as U.S. Pat. No. 7,608,834, which claims priority to PCT/EP2004/012885 filed on Nov. 13, 2004, which claims priority to EP 03292901.0 filed Nov. 21, 2003.

Figure 1A:
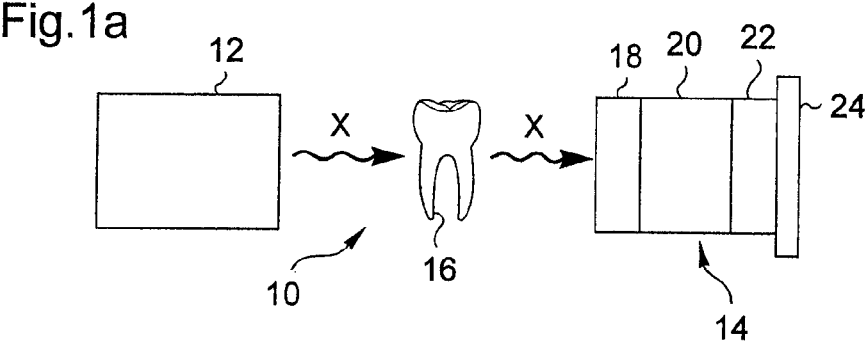
FIG. 1a is a partial schematic view of a dental radiology apparatus according to the invention during the taking of an image of a tooth.

As represented in FIG. 1a, an x-ray dental radiology apparatus 10 comprises an x-ray source 12 placed outside a patient's mouth and an intraoral radiation sensor 14 placed in a patient's mouth, behind a tooth 16, and which is capable of receiving the x-rays that have passed through the tooth.

The sensor 14 comprises, in the propagation order of the radiation, a scintillator 18 that converts the x-rays that have passed through the tooth into visible light, a fiber optic plate 20 that, on the one hand, includes metal particles intended to absorb the part of the x-rays received by the scintillator and not converted into visible light and, on the other hand, conducts the visible light thus converted to a detector 22. This detector is mounted on a ceramic substrate 24 and converts the visible light from the glass fibers into one or more analog electrical signals.

The various components of the sensor 14 are assembled together, for example, by gluing.

The scintillator 18 is, for example, made from gadolinium oxysulfide.

Alternatively, it can be made from cesium iodide, lutetium crystals or any element having the property of converting x-rays into visible light.

The fiber optic plate 20 is, for example, marketed by SCHOTT with the commercial reference 47 A or by HAMAMATSU with commercial reference XRS.

The biCMOS detector 22 is an APS type detector (Active Pixel Sensor) using biCMOS manufacturing technology, i.e. using both NMOS and PMOS transistors, as against passive pixel detectors. For further details on the biCMOS detector, document EP 0 858 111, for example, may be referred to.

An active pixel integrates amplification means of the electrical charge collected on the light sensitive pixel element.

The amplified electrical charge held by an active pixel is referred to in the rest of the description as "data value" and is representative of the quantity of light captured by the pixel.

Figure 2:
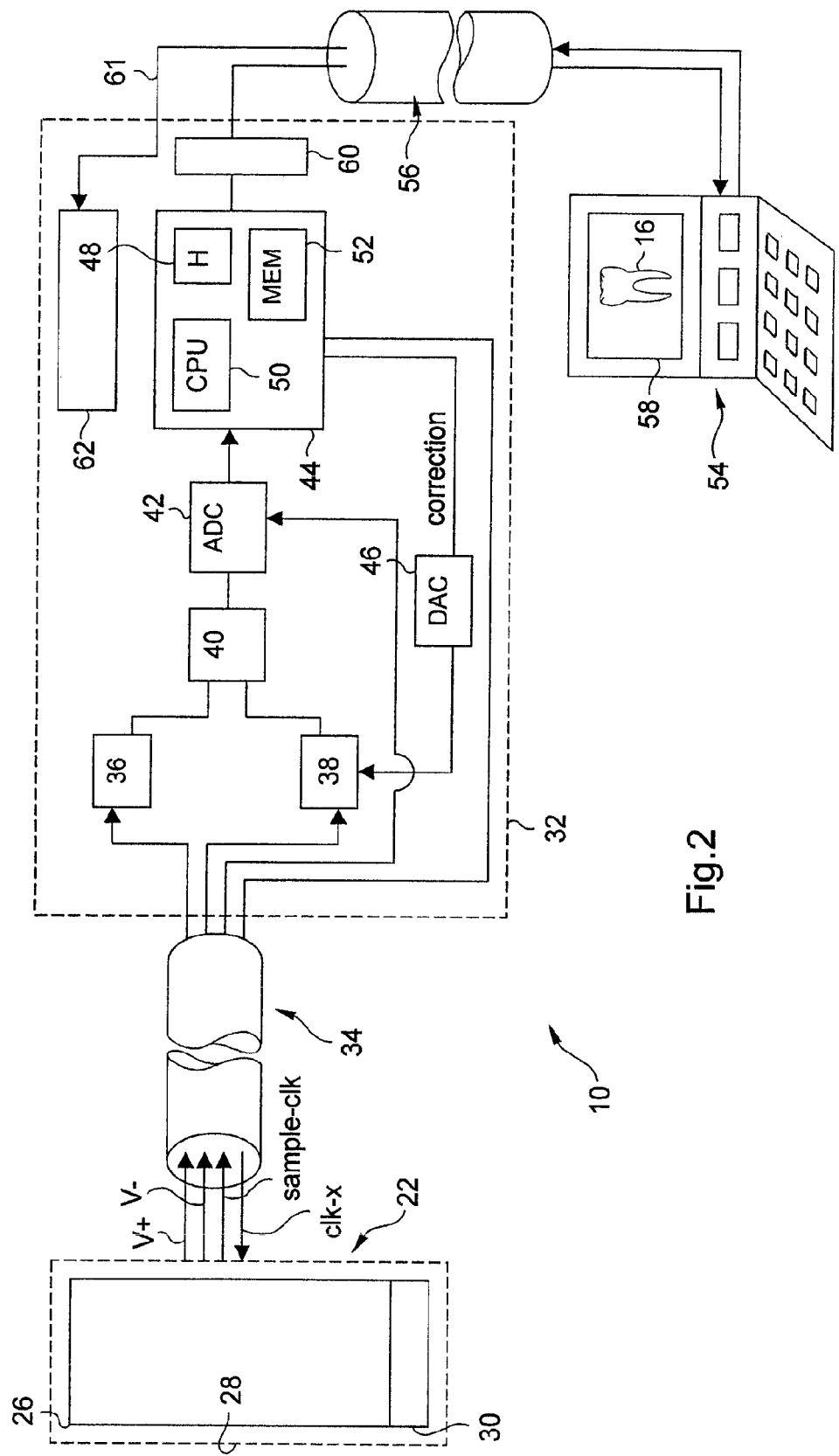

The biCMOS detector 22 represented in FIG. 2 is a chip produced on a silicon substrate 28 according to the biCMOS manufacturing technology and that includes an active pixel array 26 and a sequencer 30 integrated on the same substrate.

Figure 1B:
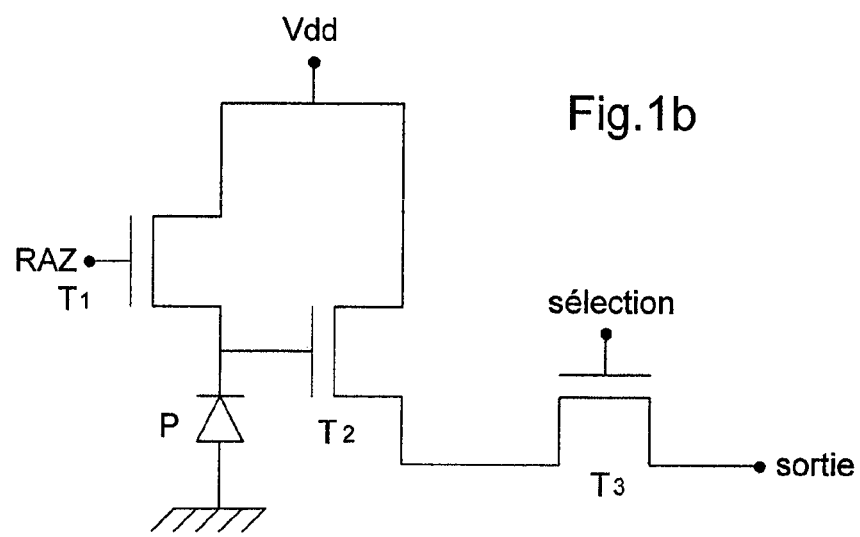
FIG. 1b illustrates a conventional representation of an active pixel using three transistors and a photodiode.

The pixels structure is, for example, the known structure illustrated in FIG. 1b and utilizing three transistors T1, T2, T3 and a photodiode P.

Preferably, the photodiode has a shape suited to optimize the pixel's fill factor, while guaranteeing sufficient channeling of the charges generated at the photodiode by the impact of photons.

Indeed, the shape of the photodiode has to enable the reliable separation of the pixels one from another to prevent the charge generated at one pixel from being collected by one of the adjacent pixels (crosstalk).

However, it should be noted that the shape of the photodiode is not to occupy too great a part of the pixel's surface area to prevent the fill factor from being decreased.

The sequencer 30 is capable of generating several control signals to control the array.

To do this, the sequencer receives one or more signals external to the sensor and from which the various array control signals are generated.

The radiology apparatus 10 comprises an electronic module 32 remote from the sensor 14 and thus the detector 22 of FIG. 2 and which is linked to this sensor by a wire link 34 that is a cable.

For example, the cable is of the multi-wire or multi-strand type, the high-frequency signals (clock, video, etc.) can optionally be channeled by coaxial cables with the assembly being shielded by a ground braid.

The above-mentioned external signal(s) is(are) generated in the electronic module 32 and transmitted using the cable 34 to the detector 22 and, more particularly to the latter's sequencer 30.

One of the external signals is, for example, a unique clock signal Clk-x, for example having a frequency of 12 MHz and from which many internal signals required for the operation of the array 26 will be generated by the sequencer.

It is especially advantageous to arrange the sequencer in the detector 22 and not in the electronic module 32, because the single transmission of a restricted number of signals including the unique clock signal coming from the module 32 is enough.

Indeed, if the sequencer were arranged in the electronic module 32, it would then be necessary to transmit by the cable 34 very many signals intended to control the array, which would cause additional noise, especially because of the crosstalk created between the various signals transmitted in the cable.

In this way, arranging the sequencer in the detector 22, and especially on the same substrate as the array, enables the detector's signal-to-noise ratio to be improved.

In the same way, the number of wires running in the cable is also reduced, which enables the use of a more flexible cable than if the latter has to carry the many control signals required to operate the array.

This is also advantageous insofar as the cable 34 leaves the patient's mouth when the sensor is placed inside, behind a tooth, and it is therefore necessary to have a cable as flexible as possible to minimize the inconvenience caused to the patient.

It may be noted that the integration of the sequencer on the same substrate as that of the array enables the detector's overall dimensions to be reduced, and thus the sensor's, which is a prime requirement for an intraoral sensor.

Indeed, a sequencer produced as a quite separate component apart from the detector's chip would inevitably lead to a more bulky sensor and thus to more inconvenience for the patient.

The reduction of the number of signals to be generated by the sequencer tends to make it less bulky.

It may be noted that the electronic module 32 is placed at a distance from the sensor of at least 50 cm so as to not inconvenience the patient or even the dentist and at a maximum distance of about 2 m from the sensor for reasons that are to be developed later.

As will also be seen below, one or more analog output signals are produced in the sensor and transmitted by means of the cable 34 to the electronic module 32 wherein they undergo several processes.

In particular, the module 32 includes two amplification units 36 and 38 which each amplify one of the analog output signals that it receives in input and a filtering unit 40 of the two previously mentioned signals.

Optionally the unit 40 can be designed to produce a single analog output signal based on the two output signals, in addition to the filtering function.

The filtered analog output signals are then joined into a single analog signal that is converted into a digital signal in an analog-digital converter 42 and transmitted to a central processing unit 44.

The central processing unit 44 includes more particularly a clock 48, a microprocessor 50 and a memory 52.

This processing unit 44 performs, among other things but not exclusively, operations of putting the detector into operating mode, as opposed to the standby periods; points the digitized signal to the output interface 60 described below; manages a memory 52 intended, for example, to contain the list of defective elements of the array 26 of the detector 22 or the detector's serial number; looks in the digitized video signal for data characteristic of the presence or not of x-rays; and manages the activation device 100 described later.

It may also be noted that a correction applied to one of the analog signals amplified by the unit 38 by means of a digital correction signal that comes from the central processing unit 44, is converted into an analog correction signal by a digital-analog converter 46 and is then applied to the unit 38.

The unit 38 performs the function of a subtractor amplifier.

The radiology apparatus 10 also includes a processing and display unit 54 remote from the electronic module 32 and linked to the latter by means of a wire link 56 which is, for example, a cable.

The processing and display unit 54 is, for example, a computer that receives the output signals of the sensor 14, once digitized and processed in the electronic module 32, in order to carry out on the latter appropriate image processing that is known to those skilled in the art to be able to view on the display screen 58 the image of the tooth 16 of FIG. 1.

An interface 60 in compliance with standard USB2.0 is provided at the output of unit 44, and a serial bus USB2.0 and an corresponding interface in the remote computer 46 (not shown), so that the signals delivered by the module 32 are transmitted to the remote computer 54 at high speed, for example about 480 Mbps.

The use of such an interface thus enables the high speed transmission to the computer of data that are supplied by the CMOS 22 detector and processed by the module 32.

The use of this interface is particularly well suited to the use of a high frequency clock signal, for example 12 MHz, for sampling the data collected by the array of the biCMOS detector 22, that is without having to use a buffer memory to store the data before their transmission to the computer.

Indeed, this clock signal frequency represents a good compromise between, on the one hand, too low a frequency to sample the array, which would cause an increase of the dark current between the start and end of the array sampling and, on the other hand, too high a frequency which would generate additional reading noise and disturb the detector's output signal.

Indeed, given the constraints linked to dark current development in the detector over time, the array's pixels have to be sampled at a relatively high frequency, which can be incompatible with the transmission speed permitted by standard USB1.

It should be noted that the USB2 bus of the cable 56 carries digitized image signals that are to be transmitted to the unit 54 and a single voltage signal 61 that will act to operate the CMOS detector following cleaning in a circuit 62 of the electronic module 32.

Indeed the biCMOS detector operates using a single power supply voltage, for example, 5 volts and TTL control levels, unlike a charge-coupled detector (CCD) for which four or five different voltage levels have to be generated and many clocks.

It should be noted that the generation of the various voltage levels causes the appearance of additional noise that disturbs the sensor's correct operation and that this phenomenon is thus avoided in the apparatus according to the invention.

The circuit 62 is to some extent a DC-DC converter which cleans the power voltage supplied by the USB2 bus and which also deals with the variations of the 5 volts of this bus by stabilizing it.

It may also be noted that the DC voltages generated by the converter 62 can be continuous, for example for use by the central processing unit 44, or switched, for example for use by the detector 22, which is only powered during use periods in the mouth. This switching is performed by the central processing unit 44.

It may be noted that the data transmission speed on the wire link 56 has to be at least equal to that provided by standard USB2.0 in order to be able to empty the array 26 rapidly without having to make use of a buffer memory.

Figure 3:
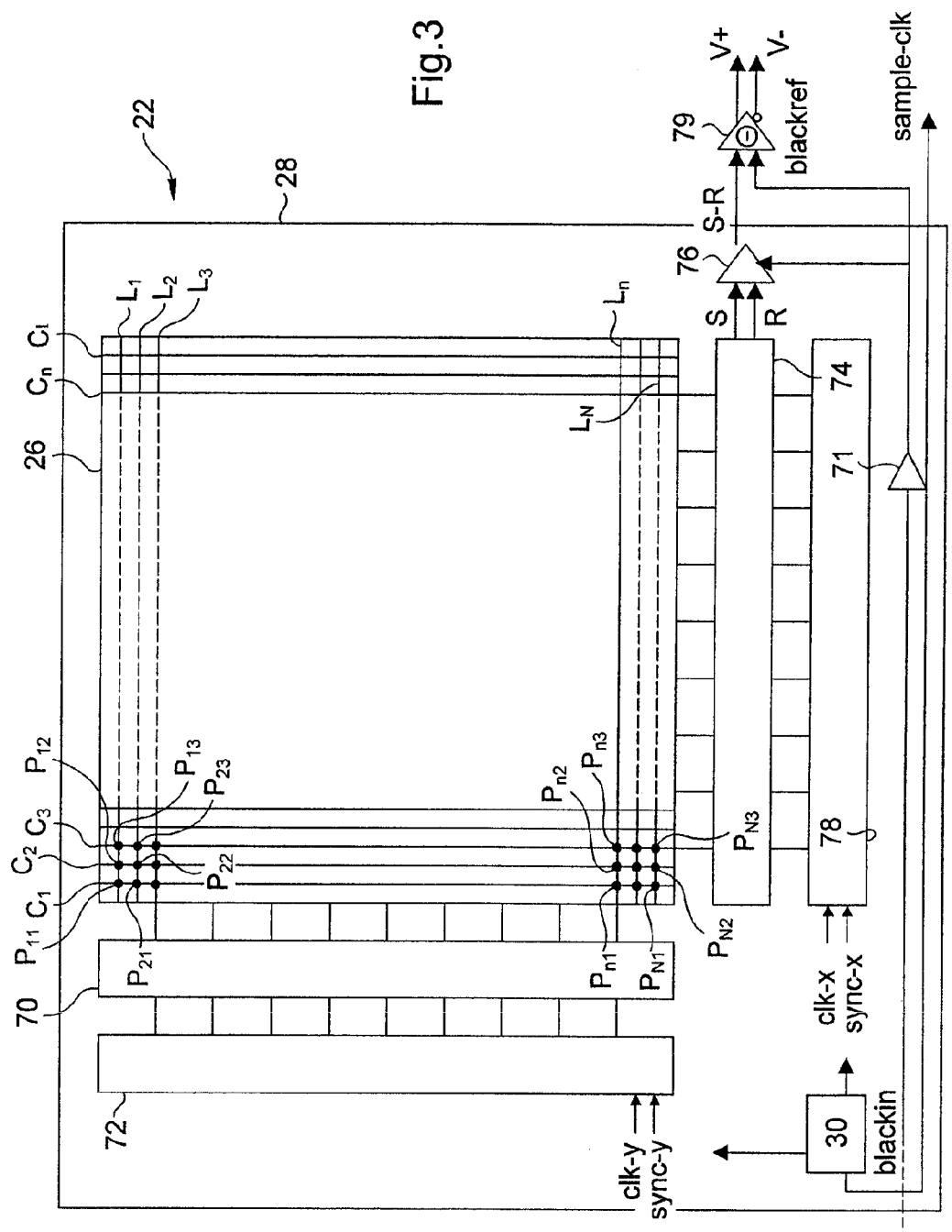
FIG. 3 is a general schematic view of the detector 22 represented in FIGS. 1a and 2.

FIG. 3 represents in a more detailed way the arrangement of the active pixel array 26 and the sequencer 30 on the common substrate 28 of the detector's chip.

The array 26 is linked to a circuit 70 for selection piloting and resetting the rows $L_1, L_2, L_3 \ldots L_n \ldots, L_N$ of the array.

A circuit 72 of shift registers controlled by the clock and synchronization signals enables the circuit 70 to be controlled for the successive operations of row selection and resetting.

The array is also connected to an amplification circuit 74 of columns $C_1, C_2, C_3 \ldots, C_n \ldots, C_I$ of the array and which multiplexes on an output amplification circuit 76 the image data captured by said array.

A circuit 78 of array column shift registers is provided to control the operation of the circuit 74 and, especially, to pilot the reading of the pixels of each array row.

As stated above, the detector receives several signals from the electronic module 32 and, especially, the signals Clk-x, Clk-y and Sync-y from which all the array's internal signals are derived.

The signal Clk-x is a clock signal, for example, at 12 MHz which acts to pilot the column shift registers and constitutes the principal clock signal from which the sequencer 30 generates all the signals, and especially the array control signals.

The control signal Sync-y acts to initialize the reading of the array.

The signal Clk-y is the control signal of the row shift registers controlling the circuit 72.

The reading of the image data captured by the array is performed as follows.

The signal Sync-y, applied at the same time as the signal Clk-y, initializes the shift registers of the array's rows and causes the selection of the first row of the array.

A first selection signal of the first row of the array, which is generated by the sequencer 30, is tripped, for example, on a rising front of the clock signal Clk-y, and controls the selection of the first row of the array.

The application of the signal Clk-x will cause the appearance of the video signal (output signal) at the detector's output.

The application of only the signal Clk-y will cause the selection of the next row of the array.

This continues until all the rows have been read, and then the combination of the signals Sync-y and Clk-y is applied again to select the first row of the array again.

For the selected row thus considered, the various data values held by each of the row's pixels having been exposed to radiation will undergo a first sampling step, also called reading step, at a rate set by the clock signal Clk-x.

Each value of the pixel's light data is stored in the column amplification circuit 74.

Following a first sampling step of the first row's pixels, a Reset signal is generated by the sequencer in order to reset all the pixels of the relevant row.

This resetting step initializes all the pixels of the selected row to a reference data value specific to each pixel.

This is a data value corresponding to an unlit pixel, also called dark data value.

After initialization of the pixels of the relevant row, a second sampling or reading step of the reference data values held by each pixel is performed, at the rate set by the clock signal Clk-x that selects the various columns of the array.

The sampled reference data values are stored in the column amplification circuit 74 where they are added to the light data values already stored and coming from the first sampling step.

The two types of data values are then multiplexed on two buses respectively, one carrying a read signal S (light data values) and the other carrying a re-initialization signal R (reference data values).

The data coming from these two buses are multiplexed on the output amplification circuit 76 according to a rate set by the clock signal Clk-x which activates the column shift registers.

An S-R output signal is created by the output amplification circuit 76 based on the difference between the read signal S and the re-initialization signal R and a reference signal that is representative of the electronic drifts intrinsic to the detector.

This reference signal comes from an input reference signal "black-in", which is a DC voltage coming from the module 32 and applied at the detector input. The reference signal "black-ref" is created as shown in FIG. 4.

Figure 4:
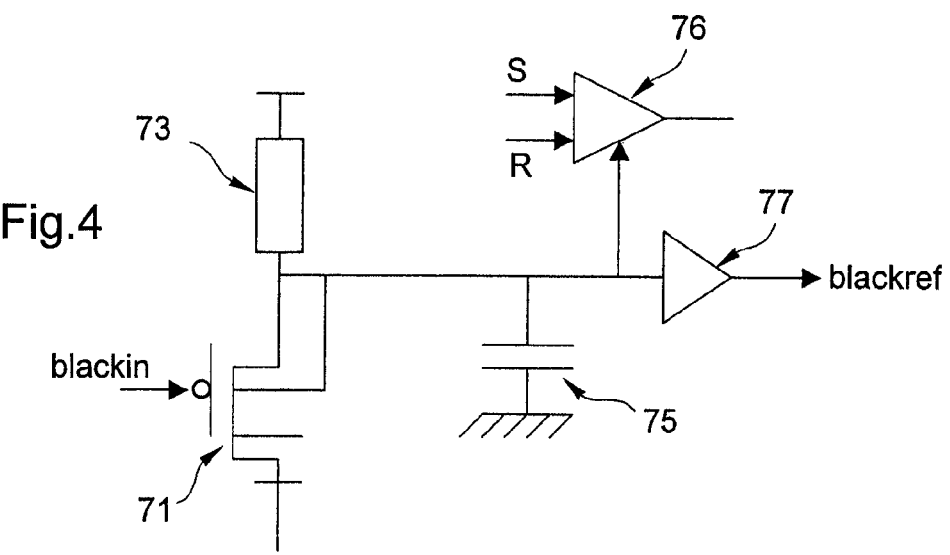
FIG. 4 is a schematic circuit illustrating the generation of the detector's output reference signal (black ref).

The circuit of FIG. 4 is representative of the way noise is generated in the detector and the black-in signal applied at this circuit's input undergoes drifts as it goes through the array.

Therefore, this circuit comprises a transistor 71 that acts as buffer memory for the black-in input signal and is also shown schematically in FIG. 3.

A resistor 73 and capacitance 75, whose values are appropriately selected according to the detector, are representative of the detector's intrinsic elements.

An amplifier 77 amplifies the signal obtained after it has undergone the distortions caused by the elements 71, 73 and 75 and the black-ref amplified signal is thus delivered at the detector's output 22.

Figure 5:
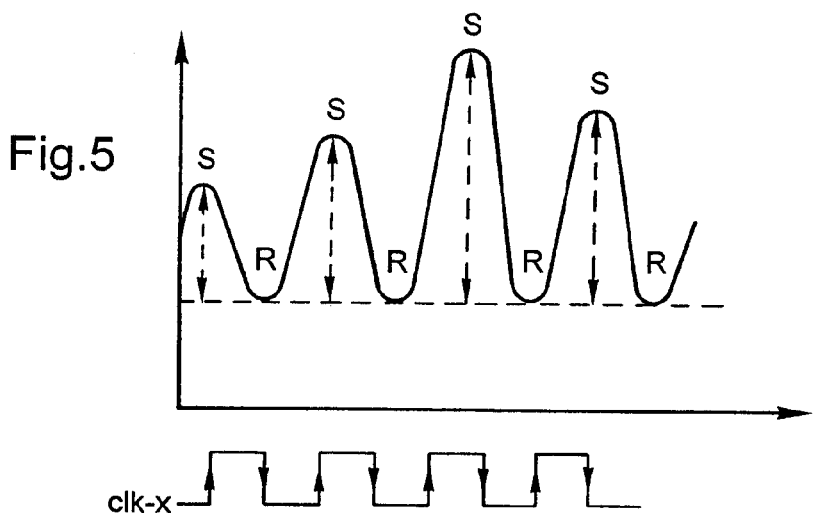
FIGS. 5 and 6 illustrate the rate of the S-R signals before and after the double sampling that is performed in circuit 76 of FIG. 3.

The signal obtained before going into the amplifier 77 ("non-amplified reference signal") is supplied to the output amplification circuit 76 where, with the clock signal Clk-x, on one of the rising or falling fronts of the signal Clk-x the strongest value of the S-R signal is selected and, on the other front, the value supplied by the non-amplified reference signal is selected, as illustrated in FIG. 5.

Thus an S-R signal is obtained whose highest values are those of the array read signal and whose lowest values are those of the non-amplified reference signal, these latter values varying over time.

Figure 6:
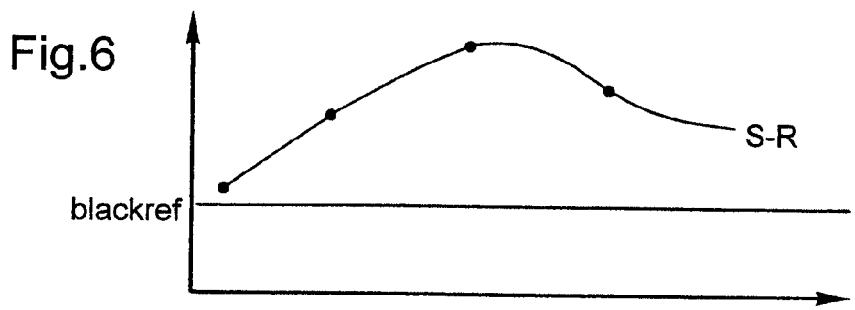

The S-R signal obtained (FIG. 6) is representative of the tooth's image data captured by the detector's pixels.

Figure 7A:
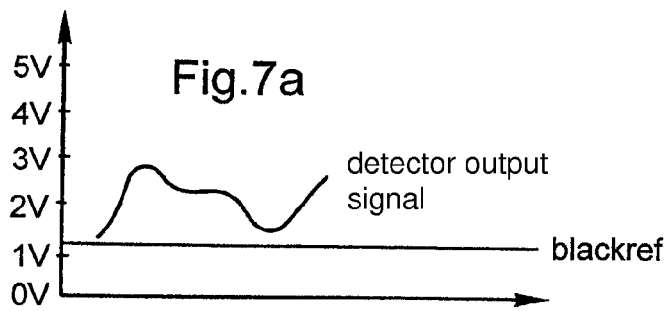
FIGS. 7a and 7b respectively represent the rate of the input and output signals of circuit 79 of FIG. 3.

FIG. 7a represents the overall rate of the R-S signal of the detector's output (FIG. 3) and the black-ref output reference signal.

As shown in FIG. 3, the analog electrical signal of the detector's S-R output is converted by a signal generator 79 into two differential analog electrical signals V+ and V−.

Figure 7B:
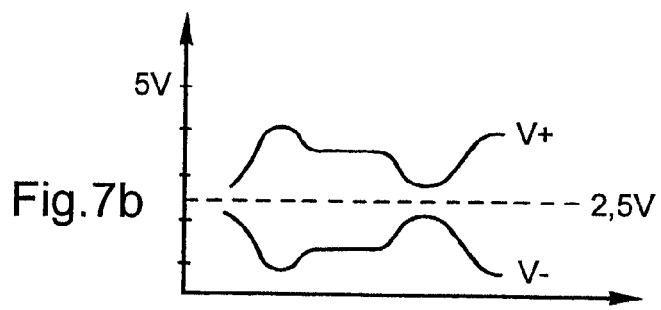

The generator 79 is a two-output amplifier which subtracts the black-ref signal from the S-R signal and delivers differential signals V+ and V- whose rate is shown in FIG. 7b.

The superimposition of the difference between the S-R signals and the black-ref output reference signal avoids any drifts due to the detector's construction that are constant over time and that vary from one sensor to another.

By transmitting the image signal from the sensor in differential form, the various disturbances it may be subject to are avoided.

Indeed, as each of the two signals V+ and V− is subject to the same disturbances, by reconstituting a single signal the disturbances found on each of the signals V+ and V− can thus be avoided, which would not be the case if only the image signal were transmitted.

Furthermore, the transmission of a differential image signal also indirectly enables the sensor's signal-to-noise ratio to be improved.

Figure 7C:
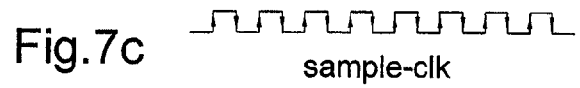
FIG. 7c represents the rate of the sampling signal Sample-clk.

A sampling signal Sample-clk is generated by the sequencer (FIG. 3) and, by construction, is perfectly synchronous with the S-R output signal insofar as the sequencer knows exactly when the data will arrive at the detector's output. The sampling signal is produced by a phase difference suited to the clock signal Clk-x and is shown in FIG. 7c.

This sampling signal which is in phase with the S-R output signal, and thus with the differential signals V+ and V−, will be transmitted simultaneously with the latter by the cable 34 intended for the electronic module 32.

The simultaneous transmission of in-phase signals will enable, inside the electronic module 32, conversion of the differential analog signals to be performed in the analog-digital conversion circuit 42 at the frequency set by the sampling signal.

By transmitting the signals simultaneously, this enables phase errors arising in the cable to be avoided insofar as a phase error affecting both the differential analog signals and the sampling signal can be compensated for.

In the same way any other disturbances affecting the signals during their transmission are avoided.

As shown in FIG. 2, the differential analog output signals V+ and V− are respectively amplified in the amplification circuits 36 and 38 before being transmitted to the filtering circuit 40.

Figure 7D:
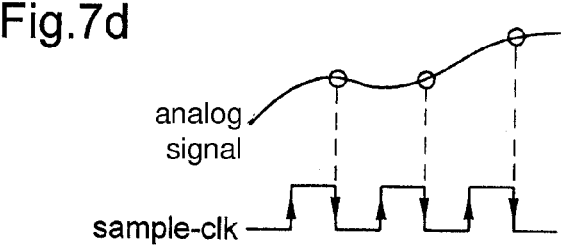
FIG. 7d schematically represents the analog-digital conversion of the video signal using the sampling signal.

The signals thus filtered are transmitted to the analog-digital converter 42 where they are summed to produce a single signal and this signal is digitized using the sampling signal Sample-clk (for example on the rising front of the sampling signal, as shown in FIG. 7d) before reaching the central processing unit 44.

In order to avoid time variation of the dark current, which is defined as being the electric current collected at the detector output when the latter is not exposed to any radiation, a correction signal is generated between two phases of exposure to radiation of the array that are, for example, successive.

It may be noted that the generation of such a signal can be regular or not over time.

Thus aside from the sensor taking a tooth image, a sampling of the data values held by the pixels of the array when this is not exposed to any radiation is carried out. The array reading signal that is generated is a correction signal.

Similarly to the above description for the output signals V+ and V−, the reading signal, in the absence of radiation, is transmitted in differential form in the cable 34 and then amplified in the amplification circuits 36 and 38 before being reconstituted as a single signal by the circuit 40 and digitized in the converter 42.

This digitized signal is introduced into the central unit 44 in which the microprocessor calculates an average value of this digitized signal which is not zero, unlike what should be obtained in the absence of radiation. This average value is injected into the analog digital converter 46 to convert it into an analog correction signal applied to one, 38, of the amplification circuits that is a subtractor circuit.

Figure 7E:
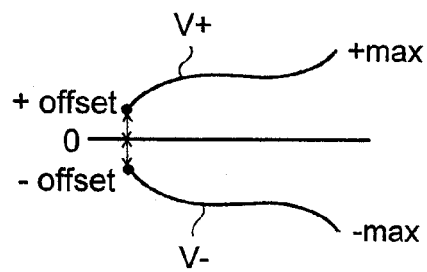
FIGS. 7e to 7g successively and schematically illustrate the correction applied to the analog signal V− to compensate for the variations of the dark current.
Figure 7F:
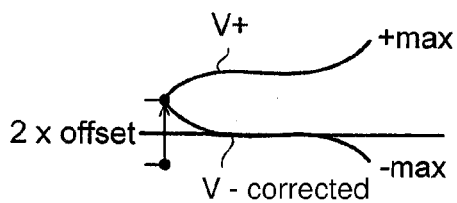

The application of this correction signal to one of the output analog signals, here the signal V−, enables this signal's amplitude to be offset by adjusting this signal towards the top as shown in FIGS. 7e and 7f.

FIG. 7e shows very schematically the rate of the differential output signals V+ and V− which are each offset in relation to the zero level by the same value.

By measuring an average value (2× offset) on the digitized correction signal and by applying it, after analog digital conversion, to the analog output signal V−, the latter is offset by a corrected value of 2× offset, as shown in FIG. 7f, to adjust it to the bottom level of the other non-corrected analog output signal V+.

Figure 7G:
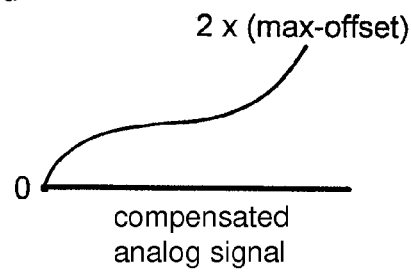

When the signal V+ and the corrected signal V− are filtered and combined, then the compensated analog signal shown in FIG. 7g is obtained that goes from zero up to a maximum amplitude of 2×(max-offset), where the "max" value designates the maximum amplitude in absolute value of each of the signals V+ and V−.

The compensated analog signal is then digitized in the circuit 42.

Thus variations due to the dark current in the array are avoided.

Figure 7H:
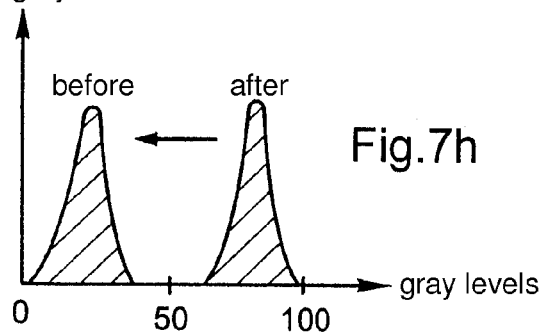
FIG. 7h shows the advantage of the dark current compensation on the gray levels obtained in the video signal.

FIG. 7h, which shows the number of pixels according to the gray levels presents in the video signal, illustrates this compensation phenomenon by demonstrating the rate of the histogram of the video signal before and after the application of a correction.

It may be noted that it is preferable to convert the correction analog signal rather than applying it directly to one of the output analog signals, as soon as the electronic module 32 receives the correction signal.

Indeed, this would require storing the correction analog signal with all the risks of drifts and/or volatility that this involves.

By performing this correction digitally, these problems are avoided and in addition the analog-digital converter is integrated into the compensation, which avoids affecting the digitizing process with a drift specific to the converter.

Further, it may be noted that a correction analog signal can also be applied to the other output analog signal V+, or even to the two signals V+ and V−.

The application of a correction to the two signals makes the process symmetrical.

The application of a correction to one of the analog output signals or to the single analog signal is adjusted according to the law of variation according to the time of the dark current of the array and the duration of use of this array.

Indeed, knowing these two settings, it is possible to plan at what moment the dark current is liable to vary most and thus to envisage performing a correction to compensate for the drifts due to these variations.

As explained above, at the time of reading the array and, more particularly, after having carried out a first sampling of the pixels of a selected row of the array, a reset signal is applied to the relevant array row by means of the circuits 70 and 72 (FIG. 3) to reinitialize the row's pixel values to the reference data values (dark data values).

However, if the reset signal varies from one row to another, an error is introduced into the data values held by the row's pixels, which results in offsets in relation to zero: the data value held by a pixel after its re-initialization is not zero as it should be in theory, but has an offset in relation to zero and, what is more, this offset can vary from one row to another.

The introduction of an additional error results in a deterioration of the signal-to-noise ratio supplied by the detector.

More especially, with such errors, a "horizontal combing" noise is introduced into the image signal produced on the screen 58 of the computer 54 (FIG. 2).

To remedy this problem, a number m of pixels of each of the array rows is first arranged to be made optically inactive, the optically inactive pixels of the various rows being equal in number (e.g. equal to 3) and arranged in the same array columns.

It may be noted that the pixels made optically inactive are arranged in the first array columns but may well also be found somewhere else, such as in its last columns.

It may be noted that the number m of optically inactive pixels can vary according to the accuracy that is required for the drift compensation introduced with the re-initialization signal.

The number m can also vary according to the size of the array.

In the embodiment example illustrated in FIG. 3, the rows $L_1, L_2 \ldots L_n \ldots L_N$ each respectively contain three "blind" pixels $P_{1.1}, P_{1.2}, P_{1.3}, P_{2.1}, P_{2.2}, P_{2.3} \ldots P_{n1}, P_{n2}, P_{n3} \ldots P_{N1}, P_{N2}$ and $P_{N3}$.

To make a pixel optically inactive, metallization or serigraphy, for example, is carried out on these pixels.

Then processing of the detector's output signal is performed after digitization by the circuit 42 (FIG. 2).

Figure 8:
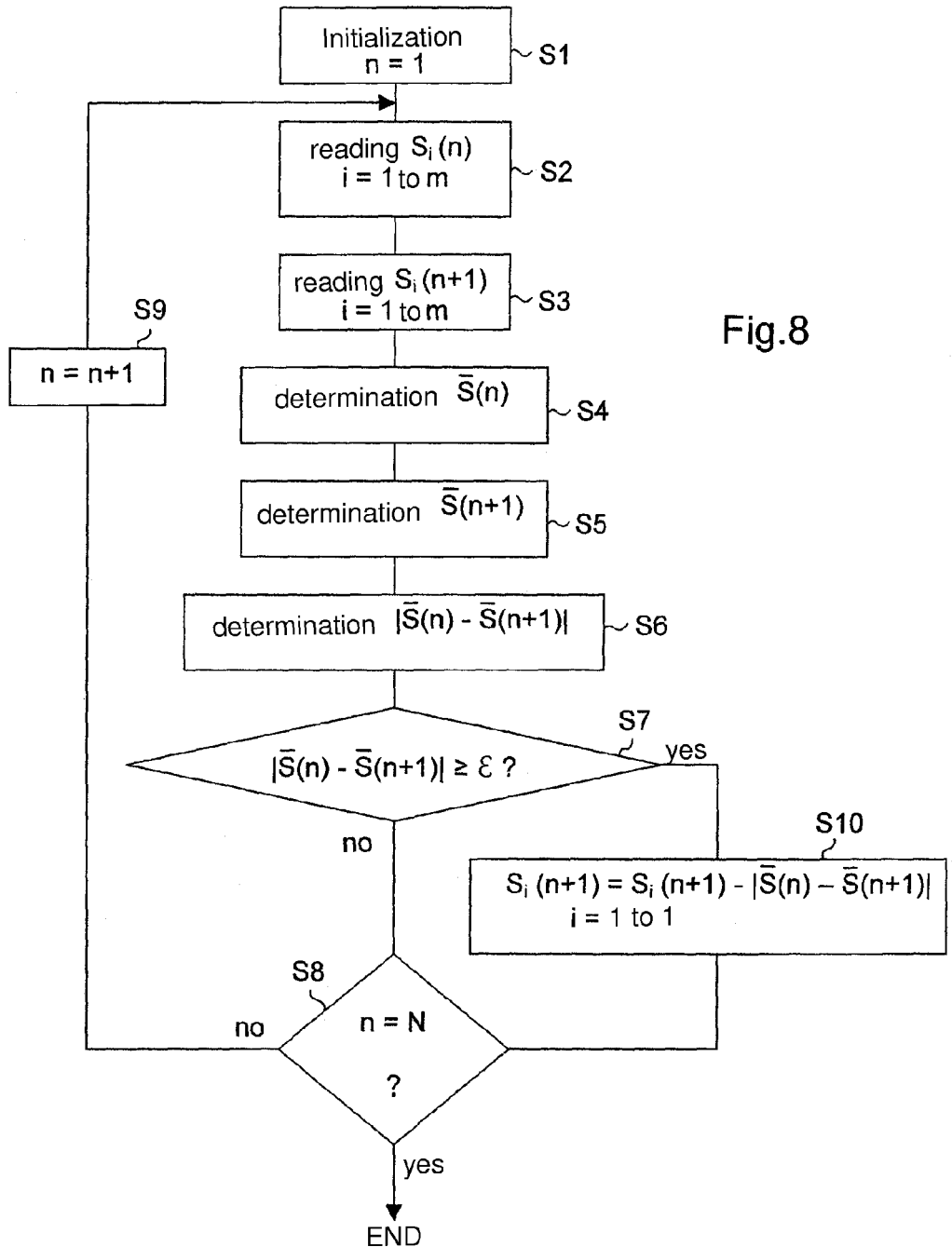
FIG. 8 is an algorithm of a computer program executed in the central processing unit 44 of FIG. 2.

The processing is applied to the signal by the central processing unit 44 by means of the processor 50 which will execute a series of instructions provided for in the algorithm of FIG. 8 which is stored in the memory 52.

This algorithm includes a first initialization step S1 during which the variable n representative of the array's rows is initialized to the value 1.

During the next step S2, the data values $S_i(n)$ of the row n of the array are read for the three blind pixels $P_{n1}, P_{n2}, P_{n3}$.

These values are read in the digitized output signal.

During the next step S3, the data values $S_i(n+1)$ are read respectively from the three optically inactive pixels $P_{n+1.1}, P_{n+1.2}, P_{n+1.3}$ of the next row n+1 of the array.

After having read the data values from the optically inactive pixels of two consecutive rows n and n+1 of the array, during the next steps S4 and S5, for each of the rows n and n+1 an average data value $\bar{S}(n), \bar{S}(n+1)$ is determined that is obtained based on the respective data values $S_i(n), S_i(n+1)$ of each row.

The higher the number m, the better the accuracy in determining the average value.

The average data value is, for example, obtained by performing arithmetic averaging.

During the step S6, the absolute value of the difference between the two previously determined average values is determined.

The next step S7 is a test that makes a comparison between the average data values $\bar{S}(n)$ and $\bar{S}(n+11)$.

In theory, one examines whether the two average values are equal but, in practice, one compares the result obtained in the step S6 with a threshold value E that takes into account, for example, the order of size of the differences that it is technically possible to detect between the average values.

When no significant difference is found between the average data values $\bar{S}(n)$ and $\bar{S}(n+1)$, then the next step S8 is a test during which one checks whether the variable representative of the number of rows n is equal to the total number N of rows in the array.

If yes, the algorithm is stopped.

If not, if array rows remain to be processed, then step S8 is followed by a step S9 during which the variable n is incremented by one unit and then the steps that have just been described are performed again.

When the result of the test made in the step S7 is positive, then it is decided to modify the data values of all the pixels of the row n+11 in the digital output signal as illustrated by the step S10.

During this step, the data value coming from each of the pixels I of the row n+11 and which is noted $S_i(n+11)$ is modified by assigning to it the absolute value of the difference determined in step S6, in order to adjust the average data value $\bar{S}(n+11)$ of the row n+11 to the average data value $\bar{S}(n)$ of the row n.

The step S10 is then followed by step S8 as described above.

By continuing in this way for each pair of consecutive rows, each of the array rows is corrected, except for the first and thus the image is homogenized row by row in order to suppress the above-mentioned "horizontal combing" noise.

It may be noted that it is also possible to make a comparison, not on two consecutive rows of the array but on three consecutive rows.

In this case, each of the data values from the m optically inactive pixels of a set of three consecutive rows of the array are read and an average data value is determined for each of these rows.

After comparison of the average data values of the three rows, according to the result of the comparison, one then decides to modify or not the data values of all the pixels of the second row in the digital output signal.

FIG. 9 shows the physical embodiment of a dental radiology apparatus according to the invention that includes the intraoral sensor 14, the electronic module 32 integrated in a case, to be described later, the two parts being interlinked by a cable 34, and a connector 80 linked to the module 32 by the cable 56.

The connector 80 is intended to work together with a complementary connector of the processing and display unit 54.

It may be noted that the cable 34 is relatively short insofar as it carries the analog signals that risk being over attenuated if the cable were too long.

This arrangement enables the constraints specific to dental radiology to be taken into account and especially because the intensity of the sensor's output signal 14 is limited by the fact that the x-ray dose going through the patient's tooth is necessarily maintained as low as possible in order not to expose the latter to too great radiation doses.

Therefore, the length 1 of the cable 34 is generally less than 2 meters.

The reduced length 1 of the cable 34 thus enables the sensor 14 signal-to-noise ratio not to be deteriorated.

On the other hand, this length 1 is generally more than 50 cm in order not to cause additional discomfort by placing it too near the patient's mouth.

However, it may be noted that the length L of the cable 56 that transmits the digital signals is not limited and can, for example, equal several meters and, in particular, be between 2 and 5 meters long.

The electronic module 32 includes a detector activation device 100 that is, for example, in the form of a pushbutton.

This device 100 is especially useful for dentists to activate the sensor 14 detector and put it into a state to receive and process x-rays that have passed through the patient's tooth 16, insofar as the module 32 is placed, when in use, within the dentist's sphere of activity.

This means that he/she can then, without having to move, hold the module 32 and press the detector's activation device 100.

This arrangement saves the dentist from moving to the remote unit 54 to click on a computer mouse with the surgical gloves that he/she used to put the sensor 14 into the patient's mouth and which are thus already contaminated, especially by the patient's saliva.

It may be noted that in the prior art, by clicking on the mouse, the intraoral sensor is activated by means of a software interface.

Thus the risks of crossover contamination with another patient are prevented insofar as the mouse is not generally part of the equipment that is disinfected after use.

After activating the sensor using the activation device 100, the dentist starts the x-ray generator 12 using a switch device 102 such as an electrical pushbutton switch (FIG. 10) that he/she has within reach.

Further, as shown in the FIG. 10, at the time of using the dental radiology apparatus according to the invention, the encapsulated electronic module is suspended from the sensor 14 when this is placed in a patient's mouth, which enables it to be within reach of the dentist when he/she is wearing gloves and has just installed the sensor in the patient's mouth.

Indeed it is possible to suspend the electronic module encapsulated in its case at the end of the cable 34 linking it to the sensor insofar as it has been designed so that its weight and dimensions enable this use.

Indeed, too high a weight would risk pulling on the cable 34, and thus exerting a pull on the sensor 14, which would be felt by the patient and cause an additional discomfort.

Furthermore, reasonable dimensions of the encapsulated module are suited to the size of an adult's hand and thus do not cause additional discomfort linked to the size, either for the dentist, or for the patient.

It may also be noted that the activation device 100 of the electronic module 32 or several activation devices can be used to execute other functions.

Insofar as a single activation device 100 is used, these other functions can be implemented by successively pressing on the latter.

Thus, when an image is being taken by the sensor or even after the image capture, it is useful to be able to supply data on the direction of orientation of the image to the image processing software installed in the remote unit 54, for example, according to whether an image of a top tooth is taken, whether the sensor is placed horizontally to take an image of an occlusion, or even whether an image of a bottom tooth is taken.

Thus, by several successive presses on the device 100, one can mark in which position the sensor has been placed by the dentist.

For example, one press on the device 100 switches on the sensor and indicates that this is taking the image of a bottom tooth, two brief presses switch on the sensor and indicate that this is taking the image of an occlusion with the sensor placed horizontally, while three successive presses switches on the sensor and indicates that the image is rotated insofar as a top tooth has been taken vertically.

Other functions such as, for example, the adjustment of image brightness or contrast, can also be controlled by activating the device 100.

Figure 11:
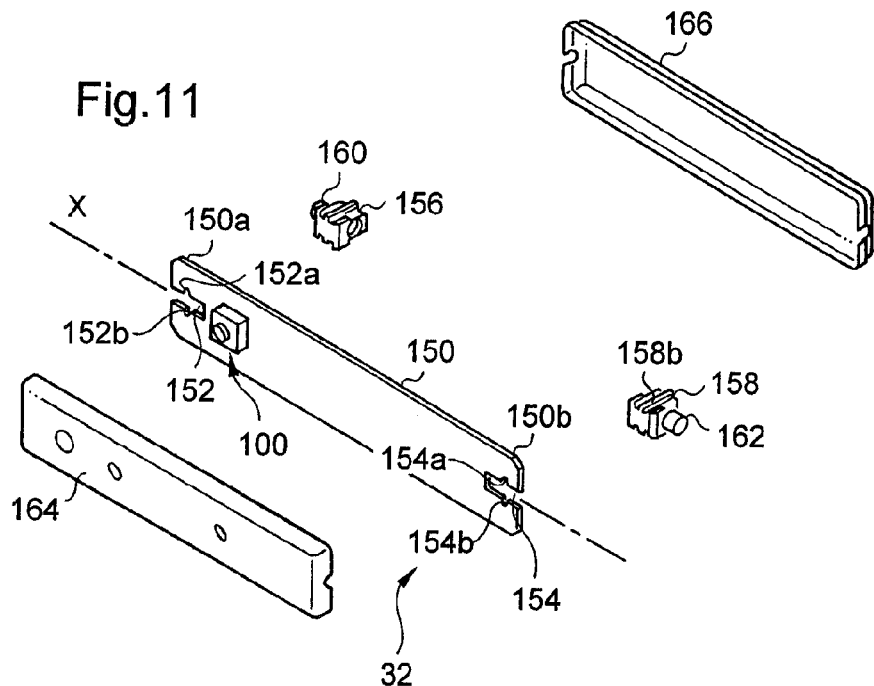
FIG. 11 is an exploded view of the electronic module 32, its anti-pull devices and metal protector half-shells.

As shown in FIG. 11, the electronic module 32 has the form of a printed circuit board 150 with overall shape elongated along a longitudinal axis X.

The printed circuit board 150 here has an overall rectangular shape and has, at each of its two opposite ends 150a, 150b that are arranged longitudinally according to the axis X, an axial cut-out 152, 154 having, for example, a rectangular shape open towards the outside of the circuit.

The axial cut-outs 152, 154 are intended to house a metal anti-pull body 156, 158 (FIG. 11) according to the circuit's longitudinal axis.

The electronic module 32 is equipped with two anti-pull devices that are each capable of working together with one of the ends of one of the cables 34 and 56, so as to prevent the removal of the corresponding cable from the electronic module and from the case by a pulling action exerted on said cable.

Each cable has a sheath (sheath 56a for the cable 56 in FIG. 12) that is coaxial with a bundle of electrical wires (bundle 56b of the cable 56).

Opposite each end of each cable that is inserted into the case, as will be seen later, the part of the corresponding wire bundle 56b, opposite the end 56c of the cable 56, is held solid with the metal anti-pull body 158.

It may be noted that everything that is described for the cable 56 and the metal anti-pull body 158 is valid for the cable 34 and the anti-pull body 156.

Each of the wire bundles (cable braid) is made solid with the corresponding metal anti-pull body by means of a cylindrical drum, marked 160 for the body 156 and 162 for the body 158, which itself is an integral part of said body.

Figure 12:
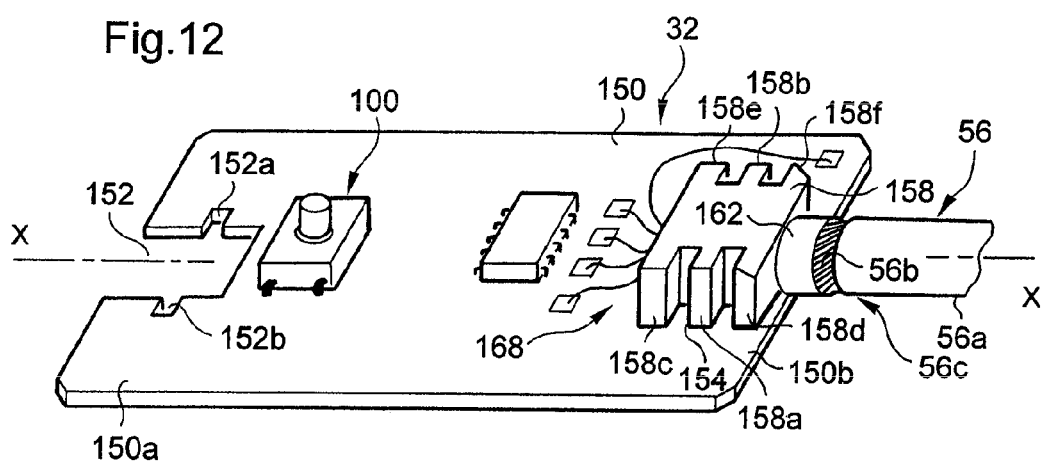
FIG. 12 is an exploded perspective view showing the installation of a metal anti-pull body and the related cable in the electronic module 32.

More particularly, the cable, for example the cable 56 of FIG. 12, is stripped at its end 56c so that the wire bundle 56b can be introduced inside the drum 162 and, then, a weld of the end part of the wire bundle can be made in the drum.

Thus, the wire bundles are made solid indirectly to the metal anti-pull body by means of the corresponding drum, but one can very well envisage welding the wire bundles directly to the body itself.

As shown in FIG. 11, the metal anti-pull bodies 156 and 158 are introduced into the corresponding longitudinal slots or cut-outs 152 and 154 perpendicularly to the longitudinal axis X of the circuit 150.

This can be explained by the fact that each metal anti-pull body is provided with fitting parts arranged on the opposite sides parallel to the direction of the end part of the wire bundle that is made solid with the body (FIG. 12), a direction that is akin to the longitudinal axis X of the circuit 150 when the metal anti-pull body is in position on said circuit.

More particularly, the fitting parts 158*a* and 158*b* of the anti-pull body 158 have the form of projections present over the whole height of the body (FIG. 13) and which work together with the complementary fitting parts arranged respectively on the opposite longitudinal edges of the corresponding cut-out.

These complementary fitting parts have the form of transversal notches that are shown in FIG. 11 and, more visibly, in FIG. 12 for the cut-out 152.

These notches 152*a* and 152*b* work together with the projecting fitting parts of the corresponding body and constitute a mortise-and-tenon type assembly.

The notches 154*a* and 154*b* of the cut-out 154 by which the metal anti-pull body 58 is introduced are shown in FIG. 11.

It may be noted that the fitting parts of the anti-pull body and the complementary parts arranged in the corresponding cut-out constitute axial holding parts of the anti-pull body, preventing any axial removal of the body in relation to the printed circuit board 150.

These fitting parts also facilitate the installation of the metal anti-pull body by an appropriate guiding in a transversal direction (FIG. 11).

The presence of the anti-pull devices means avoiding the use of electrical connectors, which is particularly advantageous.

Indeed, the use of electrical connectors would risk leading to unwanted disconnections, which is not desirable when the patient has just been exposed to a dose of x-rays and it is then necessary to expose him/her again to this radiation after having re-established the electrical connection at the electronic module.

Besides, the presence of electrical connectors equipped with sophisticated locking systems is not very desirable insofar as this would complicate the apparatus and add weight and volume to the electronic module encapsulated in its case, which is especially to be avoided.

Furthermore, the presence of an electrical connector close to the patient can become problematic for safety raisons in the case of unwanted disconnection or faulty contact.

On the other hand, the case 180 that encloses the electronic module has to be disinfected after each intervention of the dentist. But the presence of a male electrical connector and a female electrical connector requires receptacles for the connector branches and such arrangements create places that can never be sterilized, at least satisfactorily.

Besides, leak tightness problems risk arising during sterilization, which is not acceptable.

Figure 13:
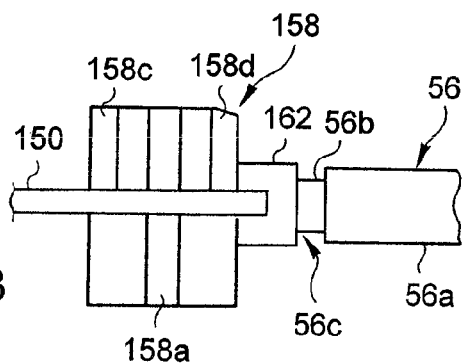
FIG. 13 is a partial schematic view of one of the ends of the electronic module equipped with an anti-pull body and a related cable.

Each anti-pull body is also provided, on its two parallel opposite sides that carry the fitting parts, with two transversal end-stop parts arranged either side of one of the fitting parts and that are referenced 158*c*, 158*d*, for those around the fitting part 158*a*, and 158*e* and 158*f* for those around the fitting part 158*b* (FIGS. 12 and 13).

These transversal end-stop parts are shorter than the fitting parts so that, when the fitting parts of each anti-pull body are introduced inside the cut-out's corresponding openings, the transversal end-stop parts come up against the cut-out's longitudinal edges to immobilize the anti-pull body in this position (FIG. 13).

It may be noted that the fitting parts arranged, on the one hand, on the metal anti-pull body and, on the other hand, on the edges of the corresponding cut-out can be reversed, in the sense that the body can be provided with longitudinal grooves and the cut-out with corresponding pins.

Other fitting parts can be envisaged (dovetail joint assembly, several notches on each edge of the cut-out, notches of different shapes, etc.).

It may be noted that the board 150 includes an activation device 100 shown in the form of a pushbutton and that enables the detector to be activated when a tooth image has to be taken.

As shown in FIG. 11, two metal half-shells 164 and 166 are arranged on either side of the printed circuit board 150 and assembled together, by means of a weld bead, to secure said printed circuit board.

These metal shells are assembled after the metal anti-pull bodies are made solid with the cables 34 and 56, after these bodies are positioned in the corresponding cut-outs of the circuit 150 and after the electrical connections 168 with the board (FIG. 12) are put into place.

It may be noted that the metal anti-pull bodies also act as spacers to enable the fixing of the metal half-shells.

The latter fulfill several functions:
  a first function of these metal half-shells is to ensure electrical continuity across the two cables 34 and 56;
  a second function is thus to provide a Faraday cage for electromagnetic compatibility purposes;
  a third function of these half-shells is to mechanically protect the electronic module 32.

Figure 15:
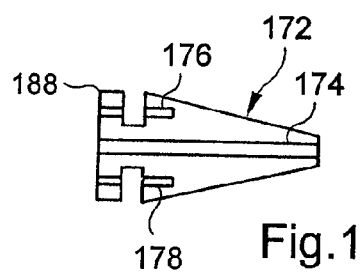
FIG. 15 is a partial schematic view of one of the end sleeves represented in FIG. 14.

Two end-sleeves 170 and 172 are provided to enable the routing of the corresponding cables 56, 34 by means of a longitudinal conduit 174 (FIG. 15).

These sleeves, such as the sleeve 172 of FIG. 15, include longitudinal recesses 176, 178 which lend them some flexibility. This flexibility prevents shearing of the cable that could occur following the repeated handling and distortion it undergoes.

These sleeves also ensure the leak tightness of the cable and the case interior.

Figure 14:
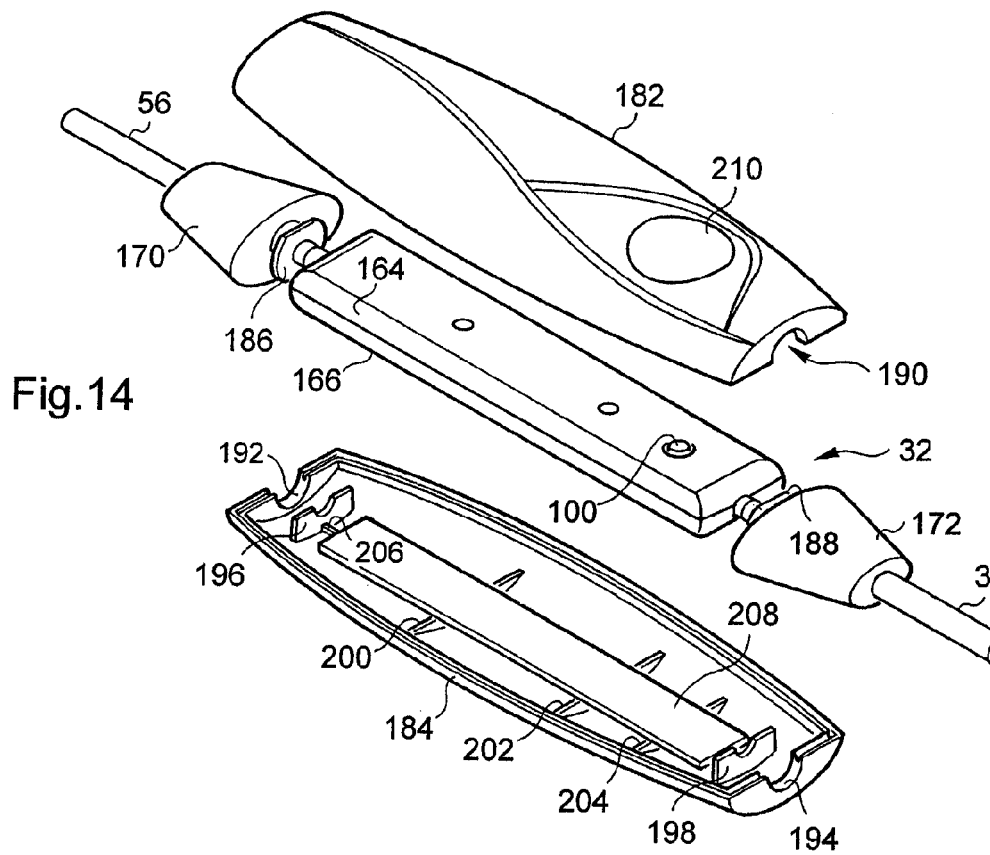
FIG. 14 is an exploded perspective view of the various elements housed inside the case 180.
Figure 16:
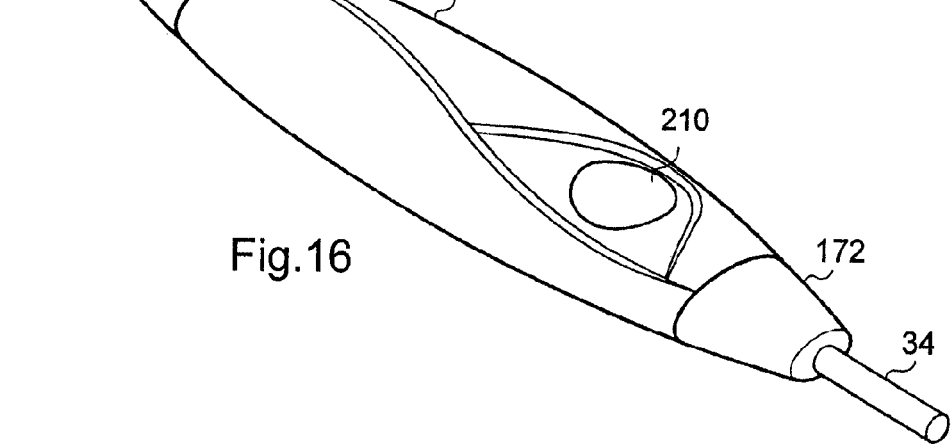
FIG. 16 is a schematic perspective view of the various parts of FIG. 14 once assembled.

The case 180 shown in FIG. 16 and which encapsulates the electronic module 32 already protected by the two metal half-shells 164 and 166 has two plastic parts forming a cover 182, 184 (FIG. 14).

These two parts with overall elongated and more particularly oblong shape are assembled together, for example, by gluing or US welding so as to enclose the electronic module 32.

One may note the presence on each of the end sleeves 170 and 172 of a collar 186, 188 (FIGS. 14 and 15) and an opening with at least partially complementary shape made at the ends of each of the parts 182 and 184 forming the cover.

In FIG. 14, the top half-cover 182 has two openings, of which one 190 is shown, and the bottom half-cover 184 has two openings 192 and 194, both shown.

When the two half-covers are assembled on either side of the electronic module 32, the openings of each half-cover slot into the collar and the latter's body to axially hold solid the case and the end-sleeves that extend it.

The openings arranged at the ends of the top and bottom half-covers thus constitute the holding edges of the corresponding sleeves.

One may also note the presence inside the top half-cover 184 of transversal guide walls 196 and 198, which are recessed to enable the positioning of the corresponding cable.

Transversal stiffening ribs 200, 202 and 204 as well as a longitudinal rib 206, of which only one end is visible, are arranged inside the half-cover 184 to stiffen the latter.

A plate 208 is arranged at the bottom of the half-cover 184 to enable correct positioning of the electronic module protected by the two metal half-shells.

It should be noted that the top half-cover 182 has the same arrangements as those described for the half-cover 184.

The detector activation device 100 cannot be directly handled by the user for leak-tightness reasons and it is accessible to the user through a thinned zone 210 provided in the top half-cover 182 and which is designed to be distorted locally and made to press in under the user's finger pressure and return to its initial position when the pressure is no longer exerted.

According to an alternative embodiment, the thinned zone is replaced by an added button created in a flexible material, which the user will have access to and which will be attached to the half-cover 182, for example by gluing, so as to ensure the leak-tightness and not to have zones capable of causing dirt incrustation.

It may be noted that the case 180 enclosing the electronic module 32, and the axial extensions 170 and 172 of this case have external surfaces enabling them to be easily disinfected/sterilized and the forms of this external surface are of a kind not to encourage dirt incrustation.

Furthermore, the external surface of the case and its axial extensions 170, 172 is drip-proof to prevent the case interior from being contaminated.

The dental radiology apparatus according to the invention thus has a particularly simple and reliable design. The video signal supplied to the processing and display unit 54 has very high quality as the detector's signal-to-noise ratio has been considerably improved compared with the prior art.

Other alternative embodiments within the capacity of those skilled in the art can also be envisaged for the various aspects of the invention that have just been described.

The invention claimed is:

1. A method of signal processing in a dental radiology apparatus comprising an intraoral sensor that includes an active pixel array produced using biCMOS technology, the pixels being arranged in rows and columns, the sensor delivering an analog output signal produced from the data values held by the array's pixels exposed to radiation, characterized in that, the pixels of at least one array column being optically inactive, comprising:
   converting the analog output signal into a digital output signal;
   reading in the digital output signal of one or more data values coming from each optically inactive pixel of an array row;
   reading in the digital output signal of one or more data values coming from each optically inactive pixel of at least one adjacent row, the relevant pixel(s) of each of the two rows being equal in number and arranged in the same column(s);
   comparing the data value(s) read respectively for the inactive pixel(s) of a row with the data value(s) read respectively for the inactive pixel(s) of the at least one adjacent row; and
   according to the result of the comparison, decision-making as to any modification in the output signal of the data values of all the pixels of one of the rows used for the comparison.

2. The method according to claim 1, characterized in that, when the data values compared with one another are different from one row to another, the method includes a modification step, in the output signal, of the data value of each pixel of the adjacent row of the array.

3. The method according to claim 1, characterized in that the array's rows are compared two by two.

4. The method according to claim 1, characterized in that, when two consecutive array rows are compared, the modification is applied to the data values of the pixels of the second row.

5. The method according to claim 1, further comprising the following steps:
   reading of the data values $S_i(n)$, i=1 to m, coming respectively from a number m of optically inactive pixels of a first array row;
   reading of the data values $S_i(n+1)$ coming respectively from m optically inactive pixels of a second row which is the next row of the array;
   determining for each of the first and second rows an average data value $\overline{S}(n)$, $\overline{S}(n+1)$ obtained from the respective data values $S_i(n)$, $S_i(n+1)$ of each row;
   comparing the average data values $\overline{S}(n)$, and $\overline{S}(n+1)$ with one another; and
   according to the result of the comparison, decision-making as to any modification, in the output signal, of the data values of all the pixels of the second row.

6. The method according to claim 5, characterized in that, when the compared average data values differ one from another, the method includes a modification step of the data value of each pixel of the second row by assigning to each of these data values the difference between the average data values $\overline{S}(n)$, and $\overline{S}(n+1)$ to adjust the average data value $\overline{S}(n+1)$ of the second row to the average data value $\overline{S}(n)$ of the first row.

7. The method according to claim 1, characterized in that it includes a step of transmitting the analog output signal to an electronic module remote from the sensor, prior to the steps of reading the data values.

8. The method according to claim 7, characterized in that the step of converting the analog output signal is performed in the electronic module.

9. The method according to claim 1, characterized in that it includes a prior step of reception by the sensor of an x-ray having passed through at least one tooth.

10. The method according to claim 9, characterized in that it includes a later step of conversion into visible radiation of the received x-ray, the array's pixels being exposed to visible radiation.

11. A dental radiology apparatus comprising an intraoral sensor that includes an active pixel array produced using biCMOS technology, the pixels being arranged in rows and columns, the sensor delivering an analog output signal produced from the data values held by the array's pixels exposed to radiation, characterized in that, the pixels of at least one array column being optically inactive, comprising:
   means for converting the analog output signal into a digital output signal;
   means for reading, in the digital output signal, one or more data values coming from each optically inactive pixel of an array row;
   means for reading, in the digital output signal, one or more data values coming from each optically inactive pixel of at least one adjacent row, the relevant pixel(s) of each of the two rows being equal in number and arranged in the same column(s);
   a comparator supplying a comparison of the data value(s) read respectively for the inactive pixel(s) of a row with the data value(s) read respectively for the inactive pixel(s) of the at least one adjacent row; and
   decision-making means capable of providing a decision as to any modification in the output signal of the data values of all the pixels of one of the rows used for the comparison.

12. The apparatus according to claim 11, characterized in that it comprises means of modification, in the output signal, of the data value of each pixel of the array's adjacent row, when the compared values are different from one row to another.

13. The apparatus according to claim 11, characterized in that the pixels of the first three array columns are optically inactive.

14. The apparatus according to claim 11, characterized in that it comprises an electronic module remote from the sensor and including the reading means, the comparator and the decision engine.

15. The apparatus according to claim 14, characterized in that it comprises means of transmission of the analog output signal to the electronic module.

16. The apparatus according to claim 14, characterized in that the electronic module comprises the means of analog-digital conversion.

17. The apparatus according to claim 11, characterized in that the sensor has an x-ray converter that is capable of converting an x-ray having passed through a tooth into visible radiation.

18. The apparatus according to claim 17, characterized in that the sensor includes a biCMOS detector including the active pixel array and which is capable of converting at least one part of the visible radiation coming from the conversion of the x-ray into an analog electrical signal.

* * * * *

UNITED STATES PATENT AND TRADEMARK OFFICE
CERTIFICATE OF CORRECTION

PATENT NO. : 8,481,956 B2
APPLICATION NO. : 13/617217
DATED : July 9, 2013
INVENTOR(S) : Alain Boucly et al.

It is certified that error appears in the above-identified patent and that said Letters Patent is hereby corrected as shown below:

In the Specification

Column 20, Line 13    Please replace the word "(n+11).", with the word --(n+1).--

Column 20, Line 16    Please replace the word "E", with the word --$\varepsilon$--

Column 20, Line 31    Please replace the word "n+11", with the word --n+1--

Column 20, Line 34    Please replace the word "n+11", with the word --n+1--

Column 20, Line 34    Please replace the word "(n+11)", with the word --(n+1)--

Column 20, Line 37    Please replace the word "(n+11)", with the word --(n+1)--

Column 20, Line 37    Please replace the word "n+11", with the word --n+1--

Signed and Sealed this
Twentieth Day of May, 2014

Michelle K. Lee
*Deputy Director of the United States Patent and Trademark Office*